(12) United States Patent
Dahanukar et al.

(10) Patent No.: US 9,233,966 B2
(45) Date of Patent: Jan. 12, 2016

(54) PREPARATION OF TICAGRELOR

(71) Applicant: DR. REDDY'S LABORATORIES LIMITED, Hyderabad (IN)

(72) Inventors: Vilas Hareshwar Dahanukar, Hyderabad (IN); Goverdhan Gilla, Hyderabad (IN); Sreenivasulu Kurella, Hyderabad (IN); Shweta Mahajan Kulkarni, Hyderabad (IN); Raghupathi Reddy Anumula, Hyderabad (IN); Sampath Aalla, Hyderabad (IN); Yakambram Bojja, Hyderabad (IN); Ravi Ram Chandra Sekhar Elati, Hyderabad (IN); Veerender Murki, Hyderabad (IN); Venkata Annapurna Sasikala Cheemalapati, Hyderabad (IN)

(73) Assignee: DR. REDDY'S LABORATORIES LIMITED, Hyderabad (IN)

( * ) Notice: Subject to any disclaimer, the term of this patent is extended or adjusted under 35 U.S.C. 154(b) by 0 days.

(21) Appl. No.: 14/389,669

(22) PCT Filed: Apr. 5, 2013

(86) PCT No.: PCT/IB2013/052733
§ 371 (c)(1),
(2) Date: Sep. 30, 2014

(87) PCT Pub. No.: WO2013/150495
PCT Pub. Date: Oct. 10, 2013

(65) Prior Publication Data
US 2015/0073146 A1   Mar. 12, 2015

(30) Foreign Application Priority Data

Apr. 5, 2012   (IN) .......................... 1389/CHE/2012
Jun. 5, 2012   (IN) .......................... 2254/CHE/2012
Jan. 4, 2013   (IN) .............................. 41/CHE/2013

(51) Int. Cl.
| | | |
|---|---|---|
| C07D 471/00 | (2006.01) |
| C07D 487/00 | (2006.01) |
| C07D 491/00 | (2006.01) |
| C07D 487/04 | (2006.01) |
| C07C 255/46 | (2006.01) |
| C07C 209/44 | (2006.01) |
| C07C 209/48 | (2006.01) |
| C07C 253/30 | (2006.01) |
| A61K 9/14 | (2006.01) |

(52) U.S. Cl.
CPC .............. *C07D 487/04* (2013.01); *A61K 9/146* (2013.01); *C07C 209/44* (2013.01); *C07C 209/48* (2013.01); *C07C 253/30* (2013.01); *C07C 255/46* (2013.01); *C07B 2200/07* (2013.01); *C07C 2101/02* (2013.01)

(58) Field of Classification Search
None
See application file for complete search history.

(56) References Cited

U.S. PATENT DOCUMENTS

| | | |
|---|---|---|
| 6,525,060 B1 | 2/2003 | Hardern et al. |
| 7,067,663 B2 | 6/2006 | Larsson et al. |
| 7,122,695 B2 | 10/2006 | Clark et al. |
| 7,799,914 B2 | 9/2010 | Larsson et al. |
| 7,863,469 B2 | 1/2011 | Dejonghe et al. |
| 8,278,475 B2 | 10/2012 | Mitsuda et al. |
| 8,563,755 B2 | 10/2013 | Bohlin et al. |
| 2007/0173518 A1 | 7/2007 | Bohlin et al. |
| 2013/0040970 A1 | 2/2013 | Cosgrove et al. |
| 2013/0150577 A1 | 6/2013 | Khile et al. |
| 2013/0165696 A1 | 6/2013 | Khile et al. |
| 2013/0317220 A1 | 11/2013 | Nair et al. |
| 2014/0094604 A1 | 4/2014 | Kansal et al. |
| 2014/0148403 A1 | 5/2014 | Cosgrove et al. |

FOREIGN PATENT DOCUMENTS

| | | |
|---|---|---|
| CN | 102249929 A | 11/2011 |
| WO | 99/05143 | 2/1999 |
| WO | 2013/037942 A1 | 3/2013 |

OTHER PUBLICATIONS

Disclosed Anonymously, "Amorphous Forms of (1S,2S,3R,5S)-3-[7-[[(1R,2S)-2(3,4-difluorophenyl) cyclopropyl]amino]-5-(propylthio)-3H-1,2,3-triazolo[4,5,d]pyrimidine-3-yl]-5-(2-hydroxyethoxy)-1,2-cyclopentanediol", IP.com PriorArt Database[online], IP.com No. IPCOM000207885D [retrieved on Aug. 30, 2013], Electronic Publication Jun. 15, 2011, pp. 1 to 3, Retrieved from the Internet: http://ip.com/IPCOM/000207885.
Written Opinion dated Sep. 26, 2013, for corresponding International Patent Application No. PCT/IB2013/052733.
International Preliminary Report on Patentability issued Oct. 7, 2014, for corresponding International Patent Application No. PCT/IB2013/052733.
International Search Report dated Sep. 26, 2013, for corresponding International Patent Application No. PCT/IB2013/052733.

*Primary Examiner* — Jeffrey H Murray
(74) *Attorney, Agent, or Firm* — Pergament & Cepeda LLP; Edward D. Pergament; Milagros A. Cepeda

(57) ABSTRACT

Provided are processes for preparing Ticagrelor and its intermediates that are useful in the processes. Also provided are salts of Ticagrelor, their processes and solid dispersion of Ticagrelor having Ticagrelor in amorphous form.

10 Claims, 13 Drawing Sheets

PREPARATION OF TICAGRELOR

This application is a National Stage Application under 35 U.S.C. §371 of PCT International Application No. PCT/IB2013/052733, filed Apr. 5, 2013, which claims the benefit of Indian Provisional Application Nos. 1389/CHE/2012, filed Apr. 5, 2012, 2254/CHE/2012, filed Jun. 5, 2012 and 41/CHE/2013, filed Jan. 4, 2013, all of which are hereby incorporated by reference in their entireties.

INTRODUCTION

Aspects of the present application relate to processes for preparing ticagrelor and its intermediates that are useful in the processes. The present application further relates to novel salts of Ticagrelor, processes for their preparation and isolation. In addition, present application provides Ticagrelor salts, its solvates and hydrates thereof in crystalline form and/or amorphous form. The application further relates to solid dispersions and compositions of Ticagrelor.

The drug compound having the adopted name "ticagrelor" has chemical names: [1S-(1α,2α,3β(1S*,2R*),5β)]-3-[7-[2-(3,4-difluorophenyl-cyclopropyl]amino]-5-(propylthio)-3H-1,2,3-triazolo[4,5-d]pyrimidin-3-yl)-5-(2-hydroxyethoxy)-cyclopentane-1,2-diol; or (1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxyl)cyclopentane-1,2-diol; and a structure depicted by Formula I.

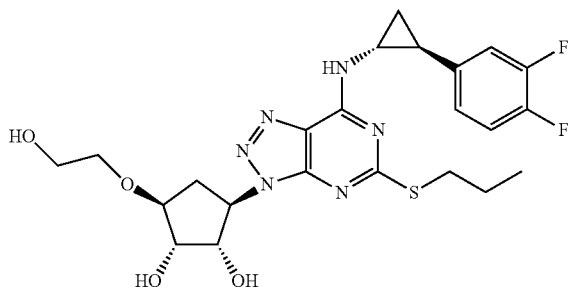

Formula I

Ticagrelor is the active ingredient in the commercially available BRILINTA® tablets for oral administration.

Ticagrelor and related compounds are disclosed in International Patent Application Publication Nos. WO 00/34283 and WO 99/05143 as pharmaceutically active $P_{2T}$ (which are now usually referred to as $P_2Y_{12}$) receptor antagonists. Such antagonists can be used, inter alia, as inhibitors of platelet activation, aggregation, or degranulation. International Patent Application Publication Nos. WO 01/92263 and WO 2010/030224 A1, WO2012085665 A2, WO2012138981 A2 and WO 2013037942 A1 disclose processes for preparing ticagrelor.

The processes for the preparation of triazolo[4,5-d]pyrimidine derivatives preferably Ticagrelor and related compounds, described in the above mentioned prior art suffer from disadvantages since the processes involve tedious and cumbersome procedures such as lengthy and multiple synthesis steps, reactions under pressure and high temperature, longer reaction times, tedious work up procedures and multiple crystallizations or isolation steps, column chromatographic purifications and thus resulting in low overall yields of the product. Ticagrelor obtained by the processes described in the prior art does not have satisfactory purity and unacceptable amounts of impurities are formed along with Ticagrelor at various stages of the processes that are difficult to purify and thus get carried forward in the subsequent steps thus affecting the purity of final compound.

Processes for the preparation of the cyclopropyl based intermediate compound of Formula VIIa are described in Patent Application Publications. WO 01/92200 A1, WO 2008/018823 A1, WO 2008/018822 A1, WO 2011/132083 A2 and WO 2012/001531 A2. These publications involve use of multi-step synthesis and/or use of chiral auxiliary for the preparation of the compound of Formula VIIa. The reported methods results in low yields, involve use of expensive chiral compounds, and further do not directly result in desired purities of the intermediate compound of Formula VIIa. Thus these processes may require an additional step of purification. Since the purity of intermediate compound play a major role in deciding the efficiency of the process for final compound, therefore there remains a need to prepare compounds of Formula VIIa of high purity and in good yield. Despite the efforts of the research aimed at finding alternative routes, it would be desirable to study methods for preparing intermediate compound of Formula VIIa, which allow overcoming the drawbacks presented by the processes described in the art.

Therefore there remains a need to prepare Ticagrelor and its intermediates of high purity and in good yield where total synthesis time is short and while overcoming the drawbacks presented by the processes described in the art. The present inventors have found an advantageous novel process for preparing enantiomerically pure trans-cyclopropyl amine derivatives which may be used in the preparation of Ticagrelor and which alleviates the hitherto problems associated with the prior art for preparing trans-cyclopropyl amine derivatives of high purity. The present inventors have additionally found an efficient process for the preparation of Ticagrelor by employing polar solvents and/or aqueous medium as reaction solvent for one of the crucial step of the synthesis. The process offers the following advantages: diastereoselectivity, enantioselectivity, simple procedures suitable for large scale production, high yields and less waste.

International Patent Application Publication No. WO 01/92262 discloses crystalline and amorphous forms of the compound of Formula (I). International Patent Application Publication No. WO 2011/067571 A1 discloses co-crystals of ticagrelor with a co-former molecule selected from glycolic acid, salicylic acid, decanoic (capric) acid, gentisic acid (2,5-dihydroxybenzoic acid), glutaric acid, vanillic acid (4-hydroxy-3-methoxybenzoic acid), succinic acid, malonic acid, or maltol (3-hydroxy-2-methyl-4-pyrone). International Patent Application Publication No. WO 2012/164286 A1 discloses co-crystal of Ticagrelor and a co-former molecule where co-former molecule is acetyl salicyclic acid.

Use of a substance for pharmaceutical purposes places high demands on the substance quality. The most efficient purification operation is crystallization. In the case of preparation of substances in amorphous form it is very difficult to achieve internationally appreciated quality criteria defined by the ICH guidelines. In those cases purification by way of preparation of acid addition salts could be very useful which on neutralization will lead to substances of improved purity. Therefore, various Ticagrelor salt forms could be used to enhance the purity of Ticagrelor.

Different salt forms of the same pharmaceutically active moiety differ in their physical properties such as melting point, solubility, chemical reactivity, etc. These properties may appreciably influence pharmaceutical properties such as dissolution rate and bioavailability. In addition, polymorphism is very common among pharmaceutical substances. It is commonly defined as the ability of any substance to exist in two or more crystalline phases that have a different arrangement and/or conformation of the molecules in the crystal lattice. Different polymorphic forms of the same pharmaceutically active moiety also differ in their physical properties such as melting point, solubility, chemical reactivity, etc.

Therefore there remains a need to prepare and characterize new Ticagrelor salt forms and their polymorphs. Further, it would be desirable to have reliable processes for producing these Ticagrelor salt forms.

Therefore the present application also relate to novel salts of Ticagrelor, processes for their preparation and isolation. It further relates to crystalline form and/or amorphous form of salts, its solvates and hydrates thereof, of Ticagrelor.

Ticagrelor exhibits low aqueous solubility. The poor solubility of drug is a significant problem in the design of pharmaceutical formulations. Ticagrelor is hardly soluble in a neutral medium such as water. Therefore, it would be desirable to provide a pharmaceutical preparation which not only releases substantially the entire active ingredient but additionally provides a fast dissolution of the active ingredient. Moreover, in particular with respect to patient compliance, it would be desirable to provide a pharmaceutical composition having a high drug load but nevertheless being easy to be prepared and stable while maintaining the beneficial properties with respect to fast solubility and bioavailability.

Solid amorphous dispersions of poorly soluble drugs are known generally to improve the solubility of drug products. However, such dispersions are generally unstable over time. Amorphous dispersions of drugs tend to convert to crystalline forms over time, which can lead to improper dosing due to differences of the solubility of crystalline drug material compared to amorphous drug material. The present invention, however, provides stable amorphous dispersions of ticagrelor with improved solubility. Moreover, the present invention provides solid dispersions of ticagrelor which may be reproduced easily and is amenable for processing into a dosage form.

SUMMARY

An aspect of the present application provides processes for preparing the compound of Formula I, embodiments comprising reacting the compound of Formula III or a salt thereof with a compound of Formula II or a salt thereof in the presence of base in a suitable polar solvent selected from alcohols, polar aprotic solvents, water and mixtures thereof, optionally in the presence of an additive to form a compound of Formula IV or a salt thereof Formula III Formula II Formula IV where $R_2$ and $R_3$ independently are hydroxy or protected hydroxy groups and X is halogen.

According to another aspect of the invention there is provided a process for preparation of compound of Formula VIIa or its salts, Formula VIIa comprising reaction of compound of Formula Xa with a Wittig reagent of Formula XI under suitable reaction conditions to afford compound of Formula XIIa.

Formula XIIa

Formula XI

Formula Xa

Another aspect of the invention provides novel intermediate compound of Formula XIIa.

The present application further relates to novel salts of Ticagrelor with hydrochloric acid, hydrobromic acid, succinic acid, fumaric acid, D-tartaric acid, L-tartaric acid, DPTTA and malonic acid. Further, relates to crystalline and/or amorphous forms of these salts and processes for their preparation.

In an aspect, there is provided a process for the preparation of salts of Ticagrelor, which includes:
  a) providing a mixture of Ticagrelor free base or its salt in a suitable solvent;
  b) adding free acid or a source of anion to the mixture of step a);

c) isolating and recovering the salt of Ticagrelor from the mixture of step b); and d) optionally drying the salt.

Another aspect of the invention provides a solid dispersion of ticagrelor prepared by dispersing ticagrelor in a carrier matrix.

Yet another aspect provides a method for preparing an amorphous solid dispersion of ticagrelor comprising: a) dissolving ticagrelor and a carrier in a solvent to form a solution; and b) removing the solvent to yield an amorphous solid dispersion.

DETAILED DESCRIPTION

Figure 1:
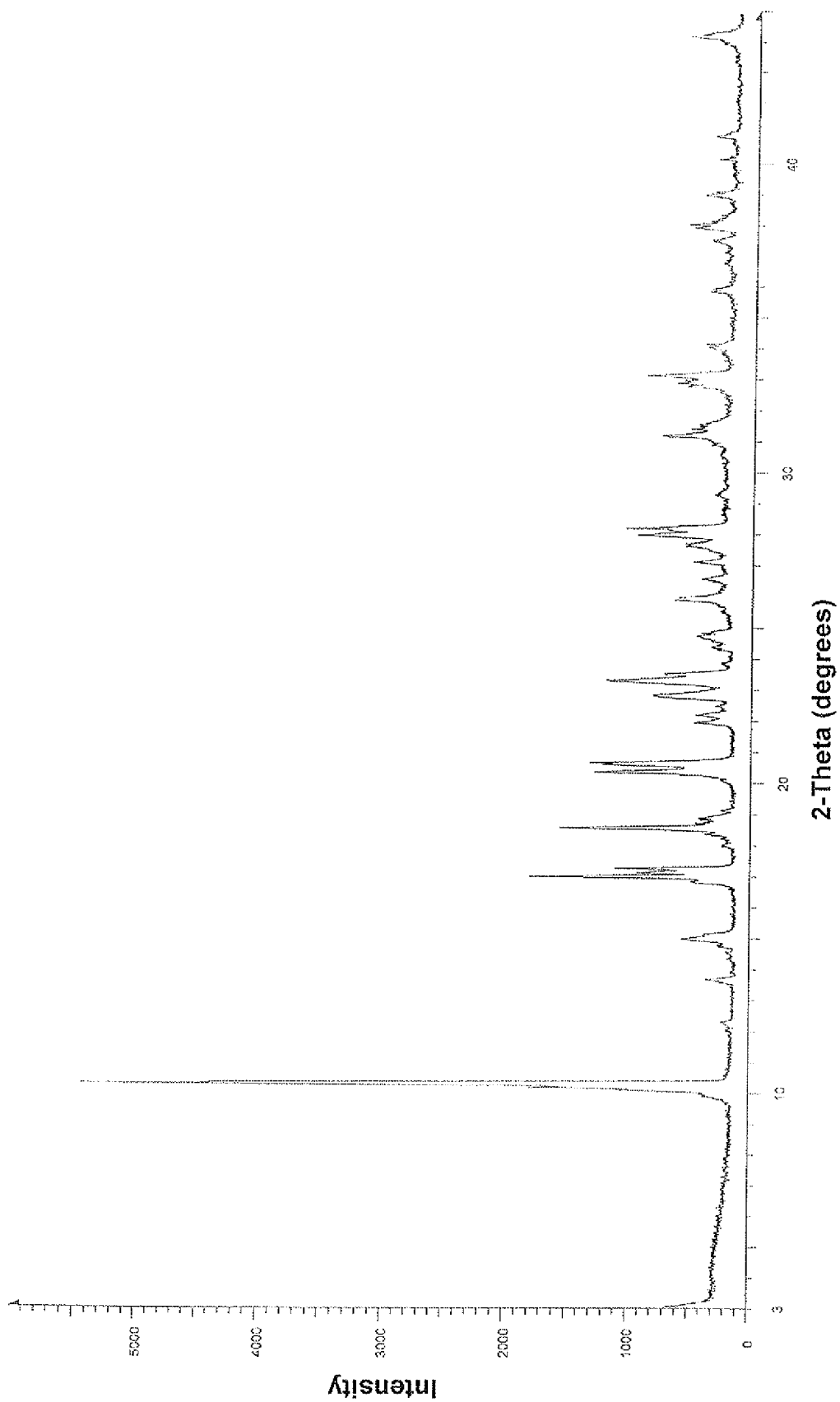
FIG. 1 is an illustration of a powder X-ray diffraction (PXRD) pattern of the compound of Formula XIIa, prepared according to Example 16.
Figure 2:
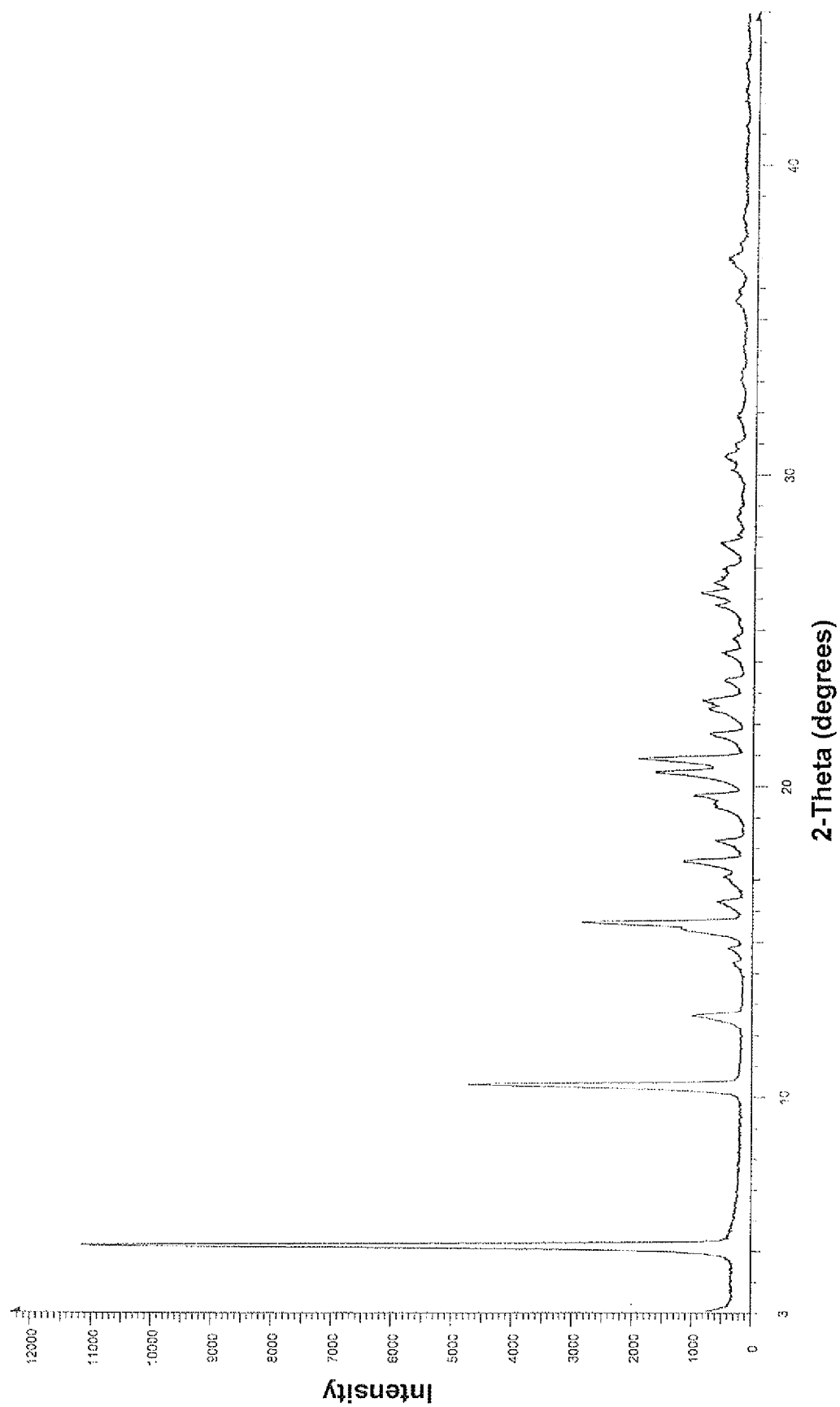
FIG. 2 is an illustration of a powder X-ray diffraction (PXRD) pattern of tartrate salt of compound of Formula VII'a, prepared according to Example 18.

Aspects of the present application provide improved processes for preparing a compound of Formula I or pharmaceutically acceptable salts thereof.

In an aspect, the present application provide processes for preparing Ticagrelor or pharmaceutically acceptable salts thereof, embodiments comprising, a) reacting the compound of Formula III or a salt thereof with a compound of Formula II or a salt thereof, in the presence of a base in a suitable polar solvent selected from alcohols, polar aprotic solvents, water and mixtures thereof, optionally in the presence of an additive to form a compound of Formula IV or a salt thereof, Formula III Formula II Formula IV where $R_2$ and $R_3$ independently are hydroxy or protected hydroxy groups and X is halogen.

The reaction can be carried out in the presence of a suitable base and suitable solvent. Suitable bases that can be employed include, but are not limited to: inorganic bases such as sodium bicarbonate, sodium carbonate, sodium hydroxide, and the like; and organic bases such as triethylamine, diisopropylethylamine, morpholine, N-methyl Morpholine, DABCO (1,4-diazabicyclo[2.2.2]octane) and the like. In a preferred embodiment, sodium bicarbonate has been employed.

Suitable polar solvents that can be employed include, but are not limited to: polar protic solvents that include alcohols, such as methanol, ethanol, 2-propanol, n-butanol, isoamylalcohol, ethylene glycol, water, polar aprotic solvents such as N,N-dimethylformamide, N,N-dimethylacetamide, N-methylpyrrolidone, dimethylsulfoxide, nitriles, such as acetonitrile and the like, and any mixtures of two or more thereof. In a preferred embodiment, water is employed as a solvent.

Mixtures of polar protic and polar aprotic solvent can also be employed.

Suitable additives include but are not limited to potassium iodide, tetrabutyl ammonium iodide (TBAI), tetrabutylammonium bromide (TBAB), sodium iodide, lithium chloride, lithium iodide and like.

A suitable salt of compound of Formula II employed in step a) is a salt of a mineral or organic acid. Suitable mineral acids for salt formation include hydrochloric, hydrobromic, hydroiodic, nitric, and sulphuric acid. Suitable organic acids include organic achiral acids such as acetic, trifluoroacetic, oxalic, succinic acid, formic acid and p-toluenesulphonic acids, and organic chiral acids such as L-tartaric acid, dibenzoyl-L-tartaric acid, and di-p-toluoyl-L-tartaric acid. Preferably, organic acid is employed and more preferably, L-tartaric acid is used.

In compounds of Formula II and IV, $R_2$ and $R_3$ independently are hydroxy or protected hydroxy groups. Some suitable protecting groups are described by T. W. Greene et al.,

*Protective Groups in Organic Synthesis, 3rd Ed.*, John Wiley & Sons, Inc., 1999, and other groups are described in the literature.

The compounds of Formulas III can be prepared by using an adaptation of literature methods, such as described in European Patent Application 508687 A1, and U.S. Pat. Nos. 7,067,663 and 7,799,914.

Compounds of Formula IV can be isolated in the form of a salt to improve the purity. A suitable salt of compound of Formula IV is a salt of a mineral or organic acid. Suitable mineral acids for salt formation include hydrochloric, hydrobromic and sulphuric acid. Suitable organic acids include organic acids such as acetic, trifluoroacetic, oxalic, succinic acid, formic acid and p-toluenesulphonic acids and organic chiral acids such as L-tartaric acid, dibenzoyl-L-tartaric acid, and di-p-toluoyl-L-tartaric acid. Preferably, organic acid is employed and more preferably, oxalic acid is used.

b) cyclizing a compound of Formula IV or its salt in the presence of sodium nitrite and suitable acid in a suitable solvent, to afford a compound of Formula V,

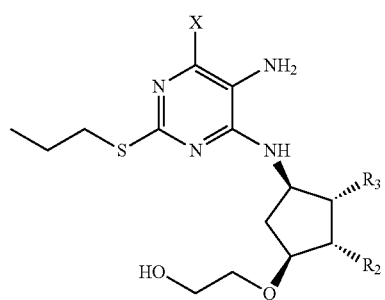

Formula IV

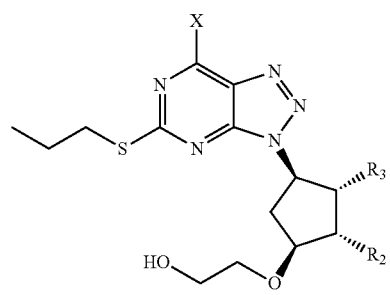

Formula V where $R_2$ and $R_3$ independently are hydroxy or protected hydroxy groups and X is halogen.

Suitable solvents employed in step b) will generally be inert to the reaction conditions. In embodiments, reaction is carried out in water or mixture of acetic acid and water. In yet another embodiment, mixture of organic solvent such as ethyl acetate and water is employed.

Suitable acid in step b) can be inorganic or organic acid. Inorganic acid selected includes but not limited to hydrochloric, hydrobromic, hydroiodic, nitric and sulphuric acid. Suitable organic acids include acetic, trifluoroacetic and like. Preferably, organic acid is employed and more preferably, acetic acid is used.

c) reacting a compound of Formula V with the compound of Formula VIIa, or a salt thereof, to form a compound of Formula VI,

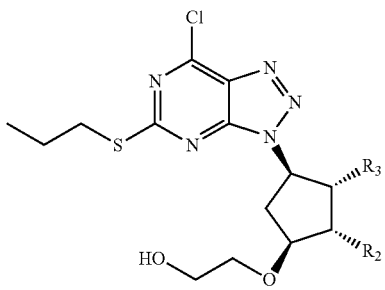

Formula V

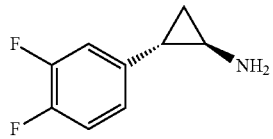

Formula VIIa

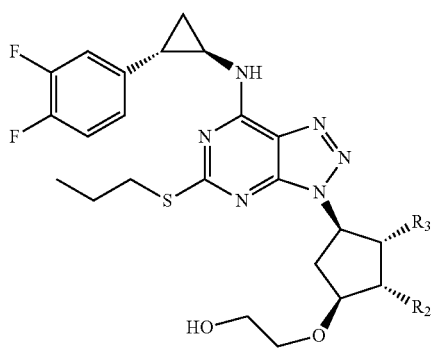

Formula VI where $R_2$ and $R_3$ independently are hydroxy or protected hydroxy groups.

The compound of Formula VIIa can be prepared by using methods known in the art or by the method included in the present application. If a salt of the compound of Formula VIIa is employed, then a free base may be generated in situ during the reaction.

The reaction is carried out in the presence of a suitable base, such as, but not limited to, organic bases like triethylamine, diisopropylethylamine, morpholine, DABCO (1,4-diazabicyclo[2.2.2]octane) and the like.

Suitable solvents will generally be inert to the reaction conditions. In embodiments, ethyl acetate is employed as a solvent.

d) optionally, deprotecting the compound of Formula VI under suitable conditions to afford Ticagrelor of Formula I.

Deprotection of a compound of Formula VI is carried out by using methods known in the art, such as by treatment with a suitable acid such as inorganic or organic acids like aqueous hydrochloric acid, aqueous sulfuric acid, and the like. Suitable solvents will generally be inert to the reaction conditions. In embodiments, for deprotection methanol is employed as a solvent.

Yet another aspect of the present application comprises a process for preparation of Ticagrelor wherein one or more intermediate compounds may not be isolated and used in organic solution itself for the next step. For example, compound of Formula III can be reacted with compound of Formula II to give compound of Formula IV which optionally without isolation on cyclization leads to compound of Formula V which optionally without isolation on subsequent reaction with compound of Formula VIIa results in a compound of Formula VI which optionally without isolation can further be converted to a compound of Formula I.

Yet another aspect of the present application provides a process for preparation of compound of Formula VII comprising,
a) 2-halo-acetylation of 1,2-difluorobenzene under Friedel-Crafts reaction conditions to afford the compound of Formula VIII,

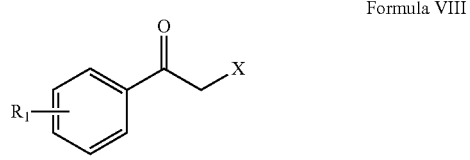

Formula VIII wherein X is halogen and $R_1$ is any suitable group which includes halogen, nitro, methoxy, methyl and like. $R_1$ can be independently selected from above groups and can be present at one or more positions on phenyl ring.

In a preferred embodiment, step a) involves a Friedel-Crafts reaction of 1,2-difluorobenzene with 2-halo-acetyl chloride. There is no particular restriction on the nature of the acid catalysts used, and any Lewis acid commonly used in reactions of this type may equally be used here. Examples of Lewis acid include, but are not limited to: aluminium trichloride ($AlCl_3$), boron trichloride ($BCl_3$), ferric chloride ($FeCl_3$), boron trifluoride ($BF_3$), boron trifluoride etherate ($BF_3OEt_2$), zinc chloride ($ZnCl_2$), aluminum bromide, aluminum chloride THF complex, or the like. The 2-halo-acetyl chloride can be selected from bromo or chloro acetyl chloride, or the like. In one embodiment, 2-chloroacetyl chloride is employed.

The step a) can optionally be carried out in presence of solvent inert to the reaction. The suitable solvent can be selected from the list of solvents provided in the application.
b) reduction of compound of Formula VIII under suitable reaction conditions to afford compound of Formula IX;

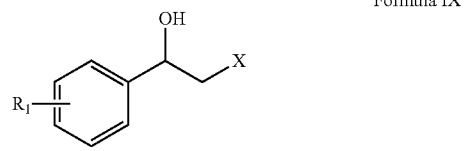

Formula IX

The reduction can be materialized by using achiral reducing agent or chiral reducing agents. The achiral reduction can be done by the methods known in literature.

In a preferred embodiment, stereoselective reduction is materialized which can be by chemical or microbial methods. In case of chemical reduction, suitable reducing agents will include those which are able to stereoselectively reduce the carbonyl group to the hydroxyl group and give an enantiomeric excess of the compound of Formula IXa.

The optically active reducing agents that can be used include, but are not limited to L-Selectride®, 2,2'-dihydroxy-1,1'-binaphthyl-lithium aluminum hydride (BINAL-H), diisobutylaluminum hydride (DIBAL-H), (+)-B-chlorodiiso-2-ethylapopinocampheylborane, (+)-B-fluorodiiso-2-ethylapopinocampheylborane, (+)-B-bromodiiso-2-ethylapopino-campheyl-borane, bis(10-methylisopinocampheyl) chloroborane, R-methyl CBS, borane-THF, borane-dioxane, borane-diethyl aniline or the like, or mixtures thereof.

Chiral reduction can optionally be done in presence of a chiral ligand. The chiral ligands that can be used is selected from the group consisting of [(R) HexaPHEMP $RuCl_2$ (R,R)-DACH], [(R)-HexaPHEMP $RuCl_2$ (R,R)-DPEN], [(R)-PhanePhos $RuCl_2$ (S,S)-DACH], [(S)-PhancPhos RuCl; (R,R)-DPEN], [(S)-MeO-Xylyl-PhanePhos $RuCl_2$ (R,R)-DPEN], [(R)-BINAP $RuCl_2$ (R)-DAIPEN], [R,R-TsDPEN (Ru) (p-cymene) Cl], and [S,S-TsDPEN (Ru) (p-cymene) Cl]. An optically active reducing agent or chiral ligand is used to attain enantiomeric selectivity and to afford the desired enantiomer in higher yield and purity.

In one embodiment, a suitable reducing agent is oxazaborolidine which may be formed by mixing of trimethoxyborane and S-diphenyl prolinol, followed by addition of borane dimethylsulfide. A suitable solvent which is inert to the reaction conditions can be selected from the list mentioned above or any other solvent.

The microbial reduction can be materialized by using suitable enzymes or microbes known in the art for said stereoselective reduction of carbonyl to hydroxy group. For example said conversion can be done using asymmetric dehydrogenase by routine adaptation of literature method.

In case of asymmetric reduction, the process may result in an enantiomeric excess of compound (IXa) over compound (IXb). Typically, the asymmetric catalytic reduction as herein defined may result in an enantiomeric excess of compound (IXa) to compound (IXb) of about 96%:4%, about 98%:2%, about 99%:1%, or higher, prior to, for example, any form of purification process such as crystallization. A crystallization purification process may improve the enantiomeric excess. A crystallized product of the asymmetric catalytic reduction may result in an enantiomeric excess of compound (IXa) to compound (IXb) of about 97%:3%, about 98%:2%, about 99%:1%, about 99.5%:0.5%, about 99.7%:0.3%, or higher. The present application may therefore result in commercially useful enantiomeric ratios of the formed compounds.

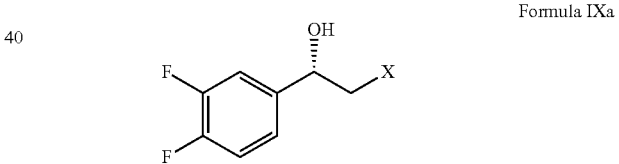

Formula IXa

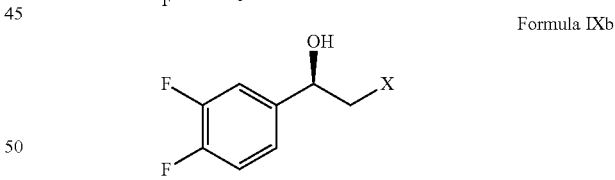

Formula IXb c) cyclization of the compound of Formula IX in presence of a suitable base to afford compound of Formula X;

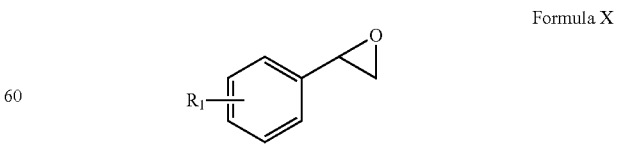

Formula X

Suitable base include but not limited to an alkali metal hydroxide such as sodium hydroxide, potassium hydroxide or the like; alkali metal carbonates and bicarbonates such as potassium carbonate, sodium carbonate, and like; alkali metal alkoxide such as sodium methoxide, sodium tert-butoxide, potassium tert-butoxide or the like; an alkaline earth metal hydride or alkali metal hydride such as lithium hydride, sodium hydride, potassium hydride, calcium hydride or the like; organolithium compound such as methyl lithium, n-butyl lithium, tert-butyl lithium or the like; an alkaline earth metal amide or alkali earth metal amide such as lithium amide, sodium amide, lithium diisopropyl amide, sodium hexamethyl disilazide or the like. In a preferred embodiment, sodium hydroxide is employed.

A suitable solvent which is inert to the reaction conditions can be selected from the list of solvents provided in the application.

Optionally, racemic compound of Formula X can be resolved to afford desired isomers by routine adaptation of methods reported in the literature.

d) reaction of compound of Formula X with a compound of Formula XI in the presence of a suitable base to afford a compound of Formula XII;

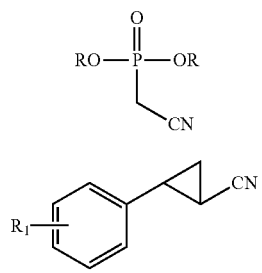

Formula XI

Formula XII

R is alkyl such as $C_1$-$C_6$ alkyl

The compound of Formula XI is a Wittig reagent which includes but not limited to diethyl cyanomethylphosphonate, dipropyl cyanomethylphosphonate, dibutyl cyanomethylphosphonate and like. In a preferred embodiment, diethyl cyanomethylphosphonate is employed.

Suitable base employed can be selected from the list provided for step c). In a preferred embodiment, potassium tert-butoxide is employed.

A suitable solvent which is inert to the reaction conditions can be selected from the list provided in the application.

Optionally, the said step can be materialized in the presence of a suitable phase transfer catalyst.

e) hydrolysis of compound of Formula XII to afford compound of Formula XIII and,

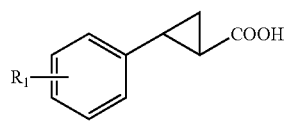

Formula XIII

The reaction can be carried out by using routinely employed hydrolysis conditions such as acid or base hydrolysis.

Suitable base employed include but not limited to an alkali metal hydroxide such as lithium hydroxide, sodium hydroxide, potassium hydroxide or the like.

Suitable acid employed include but not limited to inorganic acid such as hydrochloric acid, sulphuric acid, nitric acid, phosphoric acid, perchloric acid or the like.

In a preferred embodiment base hydrolysis is preferred. In yet another preferred embodiment, sodium hydroxide is employed.

In a preferred embodiment, racemic cis or trans isomers of cyano compound can be selectively hydrolyzed to single isomer of cis or trans stereochemistry by routine adaptation methods reported in the literature.

Optionally, compound of Formula XIII can be purified by preparing salt with a suitable base which can be organic or inorganic followed by regeneration of free acid. Preferably, purification is materialized by preparation of its amine salt and if required followed by acidification to generate the free acid of Formula XIII having enhanced purity.

f) conversion of compound of Formula XIII to compound of Formula VII;

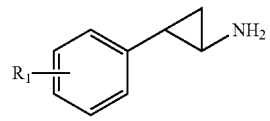

Formula VII

The said conversion can be done by methods known in the art such as by activation of carboxylic acid and its conversion to azide followed by Curtius rearrangement or by conversion of acid to amide followed by Hofmann rearrangement.

g) optionally, treatment of compound of Formula VII with a suitable acid to make acid addition salt of Formula VII';

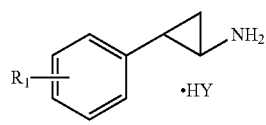

Formula VII' wherein Y is the anion of a suitable acid.

The acid employed in step g) can be chiral or achiral. To achieve the desired enantiopurity, chiral acid can be employed. Suitable chiral acid include but not limited to S-(+)mandelic acid, R-(−) mandelic acid, L-(+)tartaric acid, D-(−)tartaric acid, (−)-dibenzoyl-L-tartaric acid, (−)-dibenzoyl-L-tartaric acid monohydrate, (+)-dibenzoyl-D-tartaric acid, (+)-dibenzoyl-D-tartaric acid monohydrate, (−)-di-para-toluoyl-D-tartaric acid, (+)-di-para-toluoyl-D-tartaric acid monohydrate, (−)-di-para-toluoyl-D-tartaric acid, (−)-di-para-toluoyl-D-tartaric acid monohydrate, (1R)-(−)-10-camphorsulfonic acid or (1S)-(+)-10-camphorsulfonic acid. In an embodiment, tartaric acid is employed as a resolving agent.

To achieve the desired chemical purity inorganic acid can be employed. Suitable inorganic acid include but not limited to hydrochloric acid, sulphuric acid, phosphoric acid, perchloric acid or the like.

A suitable solvent which is inert to the reaction conditions can be selected from the list provided in the application.

h) optionally, basifying the compound of Formula VII' with a suitable base to afford the compound of Formula VII.

Suitable bases that can be employed in step h) include, but are not limited to: organic bases such as N,N-diethylaniline, triethylamine, 4-dimethylaminopyridine (DMAP), dicyclohexylamine, diisopropylethylamine, or the like; or inorganic bases such as metal hydroxides, alkoxides, carbonates, or bicarbonates. A specific example of a useful base is sodium bicarbonate. The reaction may be carried out for any desired time periods to achieve the desired product yield and purity. A suitable solvent which is inert to the reaction conditions can be selected from the list mentioned above.

Steps g) and h) are optional and can be avoided in the case of obtainment of compound of Formula VII with desired chemical and optical purity.

The invention includes any optically active substance or racemic mixture of the compound of Formulae IX, X, XII, XIII and VII. Preferably, it is optically active substance with trans-stereochemistry.

In a preferred embodiment, the present application further provides a process for preparation of compound of Formula VIIa comprising:

a) 2-halo-acetylation of 1,2-difluorobenzene under Friedel-Crafts reaction conditions to afford the compound of Formula VIII;

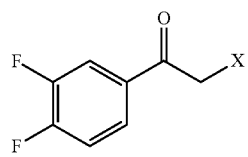

Formula VIII wherein X is halogen b) stereoselective reduction of compound of Formula VIII under suitable reaction conditions to afford compound of Formula IXa;

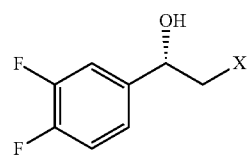

Formula IXa c) cyclization of the compound of Formula IXa in presence of suitable base to afford compound of Formula Xa;

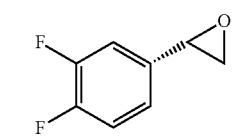

Formula Xa d) reaction of compound of Formula Xa with a compound of Formula XI in presence of suitable base to afford compound of Formula XIIa;

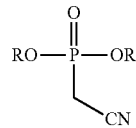

Formula XI

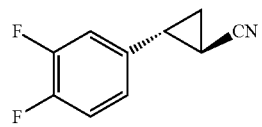

Formula XIIa

R is alkyl such as $C_1$-$C_6$ alkyl e) hydrolysis of compound of Formula XIIa to afford compound of Formula XIIIa and;

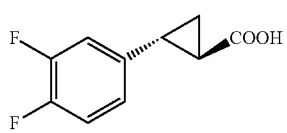

Formula XIIIa f) conversion of compound of Formula XIIIa to compound of Formula VIIa;

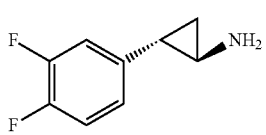

Formula VIIa g) optionally, treatment of compound of Formula VIIa with a suitable acid to make acid addition salt of Formula VII'a;

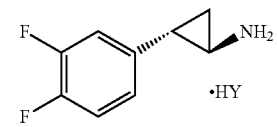

Formula VII'a wherein Y is the anion of a suitable acid.

h) optionally, basifying the compound of Formula VII'a with a suitable base to afford the compound of Formula VIIa.

The conditions suitable for above steps can appropriately be selected from the aforementioned embodiment.

In yet another aspect, the present application provides a process comprising preparation of compound of Formula X by reaction of 3,4-difluorobenzaldehye (Formula XIV) with trimethylsulfoxonium halide followed by separation of isomers to afford compound of Formula Xa, if desired by routine adaptation of literature methods.

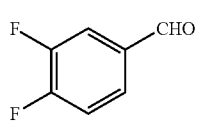

Formula XIV

In another aspect, the present application provides a process comprising reaction of compound of Formula Xa with a compound of Formula XI to afford compound of Formula XIIa.

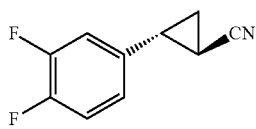
Formula XIIa

In another aspect, the present application provides the process further comprising the hydrolysis of the compound of Formula XIIa to afford compound of Formula XIIIa.

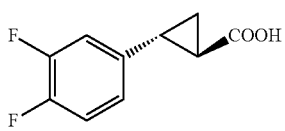
Formula XIIIa

In another aspect, the present application provides the process further comprising conversion of the compound of Formula XIIIa to desired compound of Formula VIIa.

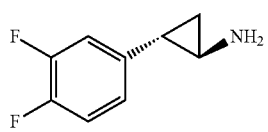
Formula VIIa

The present application also provides novel intermediate compounds of Formula XII and Formula XIIa. The said compounds in racemic as well as optically active forms and in all physical forms are included within the scope of application.

The chemical transformations described throughout the specification may be carried out using substantially stoichiometric amounts of reactants, though certain reactions may benefit from using an excess of one or more of the reactants. Additionally, many of the reactions disclosed throughout the specification, may be carried out at ambient temperatures, but particular reactions may require the use of higher or lower temperatures, depending on reaction kinetics, yields, and the like. Furthermore, many of the chemical transformations may employ one or more compatible solvents, which may influence the reaction rates and yields. Depending on the nature of the reactants, the one or more solvents may be polar protic solvents, polar aprotic solvents, non-polar solvents, or any of their combinations.

Suitable solvents inert to the reaction conditions include but are not limited to: alcohols, such as methanol, ethanol, 2-propanol, n-butanol, isoamyl alcohol and ethylene glycol; ethers, such as diisopropyl ether, methyl tert-butyl ether, diethyl ether, 1,4-dioxane, tetrahydrofuran (THF), methyl THF, and diglyme; esters, such as ethyl acetate, isopropyl acetate, and t-butyl acetate; ketones, such as acetone and methyl isobutyl ketone; halogenated hydrocarbons, such as dichloromethane, dichloroethane, chloroform, and the like; nitriles, such as acetonitrile; polar aprotic solvents, such as N,N-dimethylformamide, N,N-dimethylacetamide, N-methylpyrrolidone, dimethylsulfoxide, and the like; water; and any mixtures of two or more thereof.

The compounds obtained by the chemical transformations of the present application can be used for subsequent steps without further purification, or can be effectively separated and purified by employing a conventional method well known to those skilled in the art, such as recrystallization, column chromatography, by transforming them into a salt, or by washing with an organic solvent or with an aqueous solution, and eventually adjusting pH. Compounds at various stages of the process may be purified by precipitation or slurrying in suitable solvents, or by commonly known recrystallization techniques. The suitable recrystallization techniques include, but are not limited to, steps of concentrating, cooling, stirring, or shaking a solution containing the compound, combination of a solution containing a compound with an anti-solvent, seeding, partial removal of the solvent, or combinations thereof, evaporation, flash evaporation, or the like. An anti-solvent as used herein refers to a liquid in which a compound is poorly soluble. Compounds can be subjected to any of the purification techniques more than one time, until the desired purity is attained.

Compounds may also be purified by slurrying in suitable solvents, for example, by providing a compound in a suitable solvent, if required heating the resulting mixture to higher temperatures, subsequent cooling, and recovery of a compound having a high purity. Optionally, precipitation or crystallization at any of the above steps can be initiated by seeding of the reaction mixture with a small quantity of the desired product. Suitable solvents that can be employed for recrystallization or slurrying include, but are not limited to: alcohols, such as, for example, methanol, ethanol, and 2-propanol; ethers, such as, for example, diisopropyl ether, methyl tert-butyl ether, diethyl ether, 1,4-dioxane, tetrahydrofuran (THF), and methyl THF; esters, such as, for example, ethyl acetate, isopropyl acetate, and t-butyl acetate; ketones, such as acetone and methyl isobutyl ketone; halogenated hydrocarbons, such as dichloromethane, dichloroethane, chloroform, and the like; hydrocarbons, such as toluene, xylene, and cyclohexane; nitriles, such as acetonitrile and the like; water; and any mixtures of two or more thereof.

The compounds at various stages of the process may be recovered using conventional techniques known in the art. For example, useful techniques include, but are not limited to, decantation, centrifugation, gravity filtration, suction filtration, evaporation, flash evaporation, simple evaporation, rotational drying, spray drying, thin-film drying, freeze-drying, and the like. The isolation may be optionally carried out at atmospheric pressure or under a reduced pressure. The solid that is obtained may carry a small proportion of occluded mother liquor containing a higher than desired percentage of impurities and, if desired, the solid may be washed with a solvent to wash out the mother liquor. Evaporation as used herein refers to distilling a solvent completely, or almost completely, at atmospheric pressure or under a reduced pressure. Flash evaporation as used herein refers to distilling of solvent using techniques including, but not limited to, tray drying, spray drying, fluidized bed drying, or thin-film drying, under atmospheric or a reduced pressure.

A recovered solid may optionally be dried. Drying may be suitably carried out using equipment such as a tray dryer, vacuum oven, air oven, fluidized bed dryer, spin flash dryer, flash dryer, and the like, at atmospheric pressure or under reduced pressure. Drying may be carried out at temperatures less than about 150° C., less than about 100° C., less than about 60° C., or any other suitable temperatures, in the presence or absence of an inert atmosphere such as nitrogen, argon, neon, or helium. The drying may be carried out for any desired time periods to achieve a desired purity of the product, such as, for example, from about 1 hour to about 15 hours, or longer.

Any of the above-described compounds in racemic as well as optically active forms, and in all of their polymorphic forms, are included within the scope of this application.

The present application also relates to novel salts of Ticagrelor with hydrochloric acid, hydrobromic acid, succinic acid, fumaric acid, D-tartaric acid, L-tartaric acid, DPTTA and malonic acid. Further, relates to crystalline forms and hydrates, amorphous form of these salts and processes for their preparation.

In an aspect, there is provided a process for the preparation of salts of Ticagrelor, which includes:

a) providing a mixture of Ticagrelor free base or its salt in a suitable solvent;
b) adding free acid or a source of anion to the mixture of step a);
c) isolating and recovering the salt of Ticagrelor from the mixture of step b); and
d) optionally drying the salt.

The mixture comprising Ticagrelor free base or its salt in step a) may be a suspension or a solution. The mixture of step a) may be obtained, for example, by providing free base or a salt of Ticagrelor of any form in a solvent. The said salt may be obtained by a previous step of the process which can be a final reaction, deprotection and/or purification. If it is intended to obtain a clear solution of Ticagrelor free base or its salt, the reaction mixture can be heated to dissolution temperature that can be any temperature as long as the stability of the Ticagrelor free base or its salt is not compromised and a substantially clear solution is obtained. For example, the dissolution temperature may range from about 20° C. to about the reflux temperature of the solvent.

Solvents employed for preparation of a salts of Ticagrelor include, but are not limited to: alcohols, such as, for example, methanol, ethanol, or 2-propanol; esters, such as, for example, ethyl acetate, isopropyl acetate, or t-butyl acetate; ketones such as acetone or methyl isobutyl ketone; ethers, such as, for example, diisopropyl ether, methyl tert-butyl ether, diethyl ether, 1,4-dioxane, THF, or methyl THF; halogenated hydrocarbons, such as, for example, dichloromethane, dichloroethane, chloroform, or the like; hydrocarbons, such as, for example, toluene, hexane, heptane, xylene, or cyclohexane; nitriles such as acetonitrile; dipolar aprotic solvents such as dimethyl formamide, dimethyl acetamide, dimethyl sulfoxide or like; water; or any mixtures thereof.

Appropriate solvents or non-solvents may be determined by solubility tests in various solvents.

Step b) involves addition of free acid or source of anion to the mixture of step a). The free acid employed could be inorganic or organic. Inorganic acids include but are not limited to hydrochloric acid, nitric acid, hydrobromic acid, sulfuric acid, phosphoric acid and like; and organic acids include but are not limited to tartaric acid (D or L or DL form), succinic acid, acetic acid, fumaric acid, lactic acid (D or L or DL form), mandelic acid, trifluoroacetic acid, oxalic acid, glycolic acid, glutaric acid, carbonic acid, citric acid, formic acid, dodecylsulfuric acid, ethanesulfonic acid, ethanedisulfonic acid, methanesulfonic acid, benzenesulfonic acid, p-toluenesulfonic acid, maleic acid, malonic acid, salicylic acid, acetyl salicylic acid, naphthalene sulfonic acid and like. Optionally source of anion can be employed in step b) that could be inorganic salts or organic salts. Such salts include but are not limited to sodium sulfate, ammonium chloride, ammonium acetate, ammonium phosphate or the like. The source of anion or free acid can be directly added as solid/liquid or its mixture in a solvent can be employed. Suitable solvents are same as that employed in step a). Non-dissolved particles from a mixture of step b) can be removed suitably by filtration, centrifugation, decantation, or other techniques, such as passing the solution through paper, glass fiber, a particulate bed, or a membrane material.

The acids are employed in salt preparation-depending on whether a mono- or polybasic acid is concerned and depending on which salt is desired in an equimolar quantitative ratio or one differing therefrom.

Thus, within the acid addition salts of this invention the acid and the free compound may be substantially in 1:1 stoichiometry or one differing therefrom, such as e.g. from about 1:2 to about 2:1 stoichiometry. Non-stoichiometric ratios may also be possible, such as e.g. 1:1.5 or 1.5:1.

The reaction can be efficiently completed at room temperature or ambient temperature or if required reaction mass can be heated to elevated temperatures or up to about the reflux temperatures, and maintained for a time from about 10 minutes to about 5 hours or longer. Suitable temperatures for crystallization are from about 0° C. to about 50° C., from about 10 to about 30° C., or any other suitable temperatures may be used. Suitable times for crystallization will vary, and can be from about 10 minutes to about 10 hours, or longer.

Step c) involves isolation and recovery of Ticagrelor salt from the reaction mixture. The isolation of salts of Ticagrelor may be induced by using conventional techniques known in the art. For example, useful techniques include but are not limited to, concentrating, cooling, stirring, shaking, combining with an anti-solvent, adding seed crystals, evaporation, flash evaporation, simple evaporation, rotational drying, spray drying, thin-film drying, freeze-drying, or the like. The solid that is obtained may carry a small proportion of occluded mother liquor containing a higher percentage of impurities and, if desired, the solid may be washed with a solvent to wash out the mother liquor. Evaporation as used herein refers to distilling of solvent almost completely at atmospheric pressure or under reduced pressure. Flash evaporation as used herein refers to distilling of solvent by using a technique includes but is not limited to tray drying, spray drying, fluidized bed drying, thin film drying under reduced pressure, or thin film drying at atmospheric pressure. The recovery of salts of Ticagrelor can be done by decantation, centrifugation, gravity filtration, suction filtration and like.

Alternately, step-wise cooling can be done to ease the filtration by improving the morphology of crystalline particles.

Particularly, crystalline forms may also be obtained by heating or melting a form obtained followed by gradual or fast cooling; in this manner one polymorph or one crystalline form may be converted to another.

The salts of the present invention if desired can be purified by re-crystallization from an appropriate re-crystallization solvent or mixture of solvents by methods customary to one of skill in the art, and/or. If required, the process further comprises, at a suitable stage, removing or separating any undesired material or impurities, and finally, optionally, the salts may be washed and/or dried.

The resulting solid may be optionally further dried. Drying may be suitably carried out using equipment such as a tray dryer (VTD or ATD), vacuum oven, air oven, fluidized bed dryer, spin flash dryer, flash dryer, or the like, at atmospheric pressure or under reduced pressure. Drying may be carried out at temperatures less than about 150° C., less than about 100° C., less than about 60° C., or any other suitable temperatures, at atmospheric pressure or under reduced pressure, and in the presence or absence of an inert atmosphere such as nitrogen, argon, neon, or helium. The drying may be carried out for any desired time periods to achieve a desired purity of the product, such as, for example, from about 1 hour to about 15 hours, or longer.

Once obtained, crystals of Ticagrelor salts may be used as the nucleating agent or "seed" crystals for subsequent crystallizations of salts of Ticagrelor from solutions.

Salts of the present invention can be converted to another salts, e.g. by reaction with an appropriate acid or by means of a suitable ion exchanger. Likewise, salts obtained can be converted into the free compounds (e.g. via neutralization with a suitable base, with or without isolation of the free base, e.g. by extraction), which can in turn be converted into salts, by acidification. In this manner, formation of the selected Ticagrelor salts of the application might be an efficient way of purifying Ticagrelor free base and further, physiologically unacceptable salts can be converted into physiologically acceptable salts.

In a further aspect, the present invention relates to salts of the invention (including their solvates and hydrates) in solid forms, including amorphous, semi-amorphous, semi-crystalline and crystalline forms, as well as mixtures thereof. In a preferred aspect, salts of the present invention are Ticagrelor hydrochloride, Ticagrelor hydrobromide, Ticagrelor succinate, Ticagrelor fumarate, Ticagrelor ID-tartrate, Ticagrelor L-tartrate, Ticagrelor di-para-tolyl tartaric acid (DPTTA) and Ticagrelor malonate.

The solid form of Ticagrelor salts of the present application may be characterized by means of Powder X-ray Diffraction Pattern (PXRD). Other techniques, such as solid state NMR, Fourier Transform Infrared (FTIR), differential scanning calorimetry (DSC) may also be used.

Ticagrelor employed as a starting material for preparation of Ticagrelor salt can be obtained by any processes known in the art, including processes disclosed in U.S. Pat. No. 6,525,060 and U.S. Pat. No. 7,067,663 which are incorporated herein by reference in their entireties, as well as by other processes known in the art.

The compound of this application is best characterized by the X-ray powder diffraction pattern determined in accordance with procedures that are known in the art. PXRD data reported herein was obtained using CuKα radiation, having the wavelength 1.5418 Å and were obtained using a Bruker AXS D8 Advance Powder X-ray Diffractometer. For a discussion of these techniques see J. Haleblain, J. Pharm. Sci. 1975 64:1269-1288, and J. Haleblain and W. McCrone, J. Pharm. Sci. 1969 58:911-929.

Generally, a diffraction angle (2θ) in powder X-ray diffractometry may have an error in the range of ±0.2°. Therefore, the aforementioned diffraction angle values should be understood as including values in the range of about ±0.2°. Accordingly, the present application includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ±0.2°) of 7.9°" means "having a diffraction peak at a diffraction angle (2θ) of 7.7° to 8.1°". Although the intensities of peaks in the x-ray powder diffraction patterns of different batches of a compound may vary slightly, the peaks and the peak locations are characteristic for a specific polymorphic form. Alternatively, the term "about" means within an acceptable standard error of the mean, when considered by one of ordinary skill in the art. The relative intensities of the PXRD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of PXRD is meant to encompass that peak assignments can vary by plus or minus about 0.2 degree. Moreover, new peaks may be observed or existing peaks may disappear, depending on the type of the machine or the settings (for example, whether a Ni filter is used or not).

For example, there is provided a novel crystalline Form I of Ticagrelor hydrochloride characterized by its powder X-ray diffractogram comprising peaks at 3.38, 4.20, 5.55 and 6.44 degrees of 2θ values.

Figure 3:
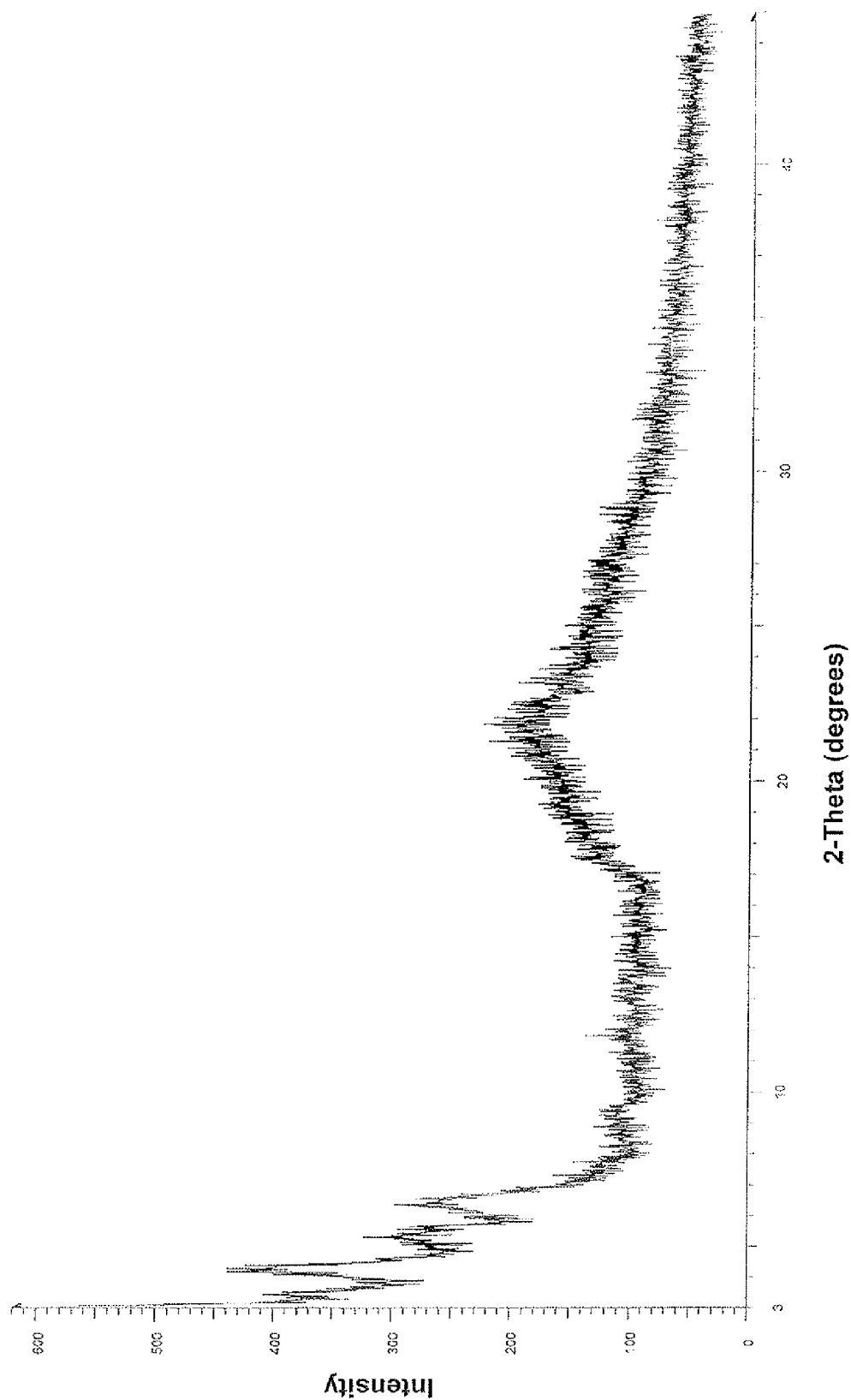
FIG. 3 is an illustration of powder X-ray diffraction ("PXRD") pattern of Ticagrelor hydrochloride Form I prepared according to example 19.

In an embodiment, there is provided crystalline Form I of Ticagrelor hydrochloride, having a PXRD pattern with peaks located substantially as shown in FIG. 3.

Figure 4:
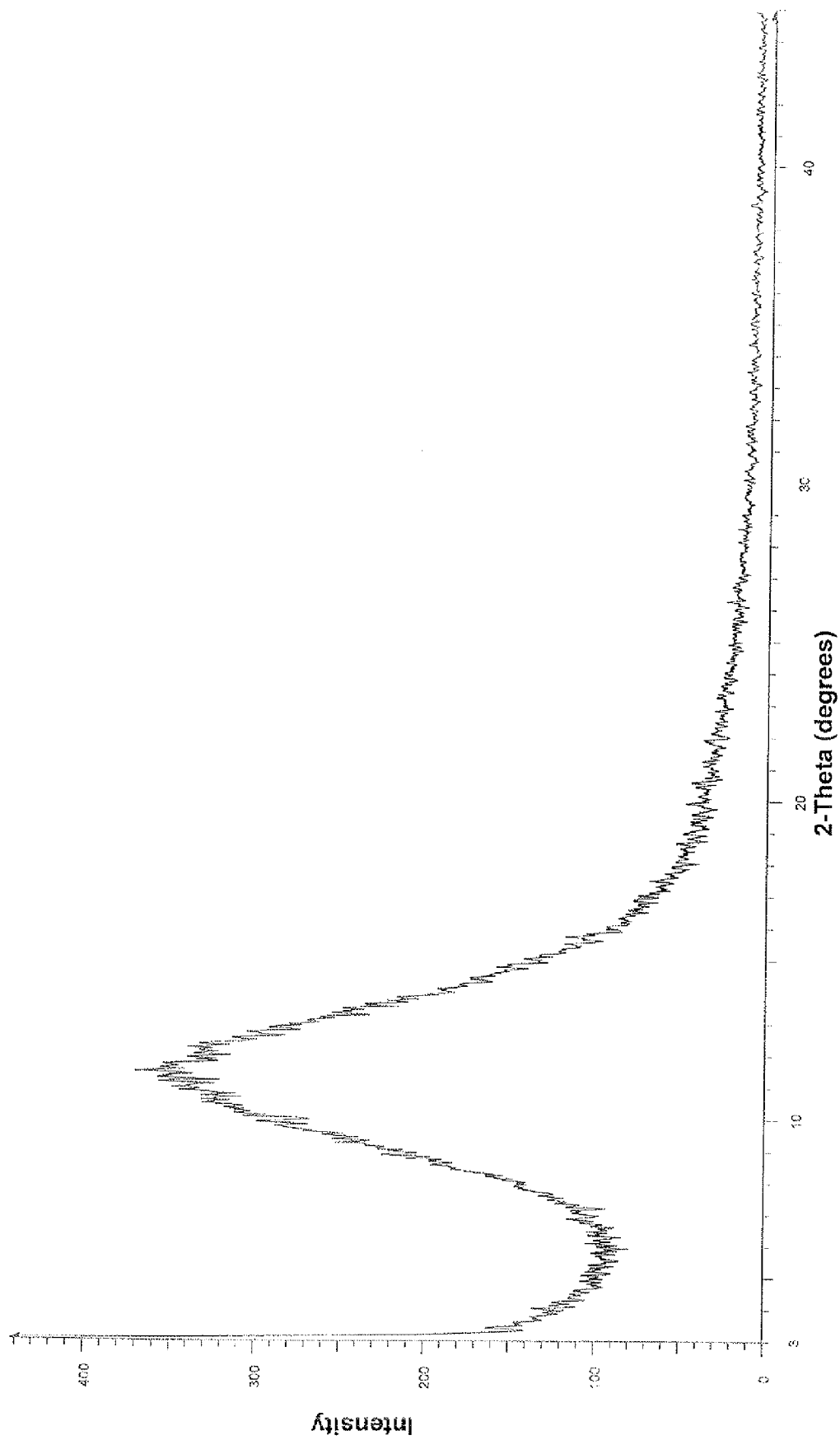
FIG. 4 is an illustration of powder X-ray diffraction ("PXRD") pattern of amorphous Form of Ticagrelor hydrochloride prepared according to example 20.

For example, there is provided amorphous form of Ticagrelor hydrochloride having a PXRD pattern substantially as shown in FIG. 4.

Figure 5:
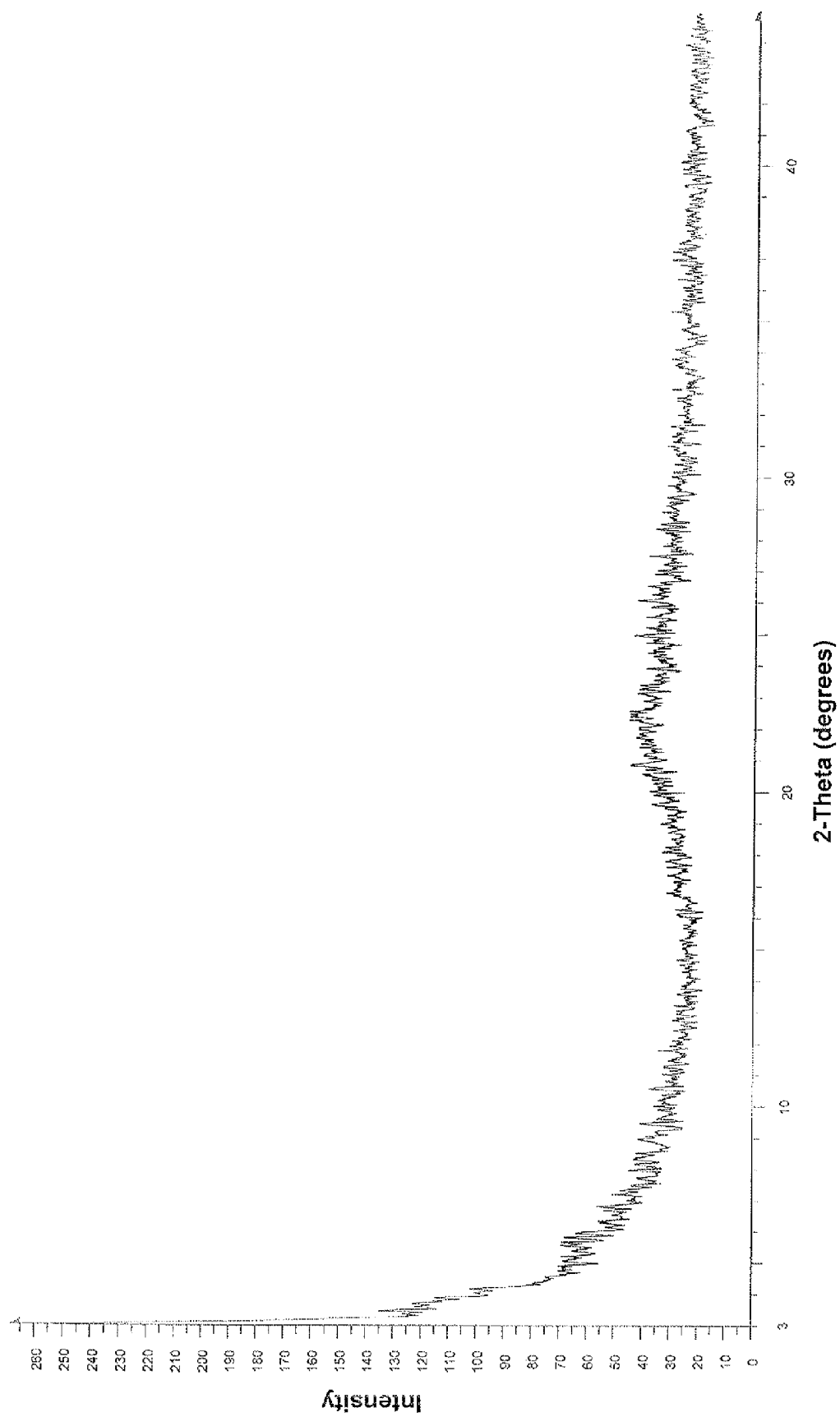
FIG. 5 is an illustration of powder X-ray diffraction ("PXRD") pattern of Ticagrelor hydrobromide prepared according to example 21.

For example, there is provided Ticagrelor hydrobromide, having a PXRD pattern substantially as shown in FIG. 5.

For example, there is provided a novel crystalline Form I of Ticagrelor succinate characterized by its powder X-ray diffractogram comprising peaks at, 26.94, 24.10, 21.79, 20.46 and 18.81 degrees of 2θ values. A PXRD pattern with two or more peaks further selected from about 32.17, 18.52, 17.61, 14.649, 13.09, 9.29, 6.14 and 5.921 degrees of 2θ values.

Figure 6:
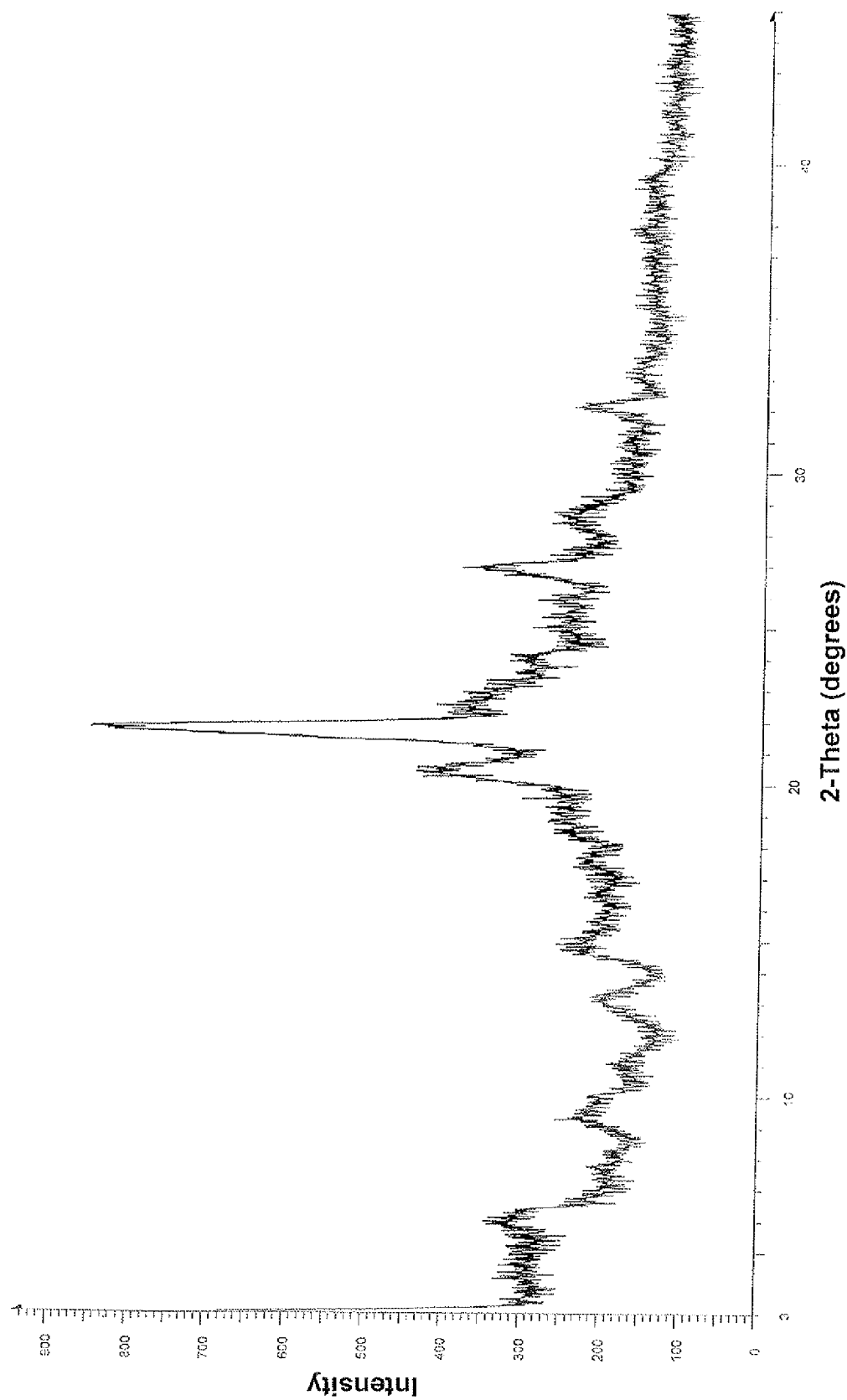
FIG. 6 is an illustration of powder X-ray diffraction ("PXRD") pattern of Ticagrelor succinate Form I prepared according to example 22.

In an embodiment, there is provided crystalline Form I of Ticagrelor succinate, having a PXRD pattern with peaks located substantially as shown in FIG. 6.

For example, there is provided a novel crystalline Form II of Ticagrelor succinate characterized by its powder X-ray diffractogram comprising peaks at, 31.69, 26.79, 26.30, 25.69, 22.09, 20.19 and 6.19 degrees of 2θ values. A PXRD pattern with two or more peaks further selected from about 42.199, 38.65, 38.21, 15.21, 13.44, 11.3, 9.54 and 9.50 degrees of 2θ values.

Figure 7:
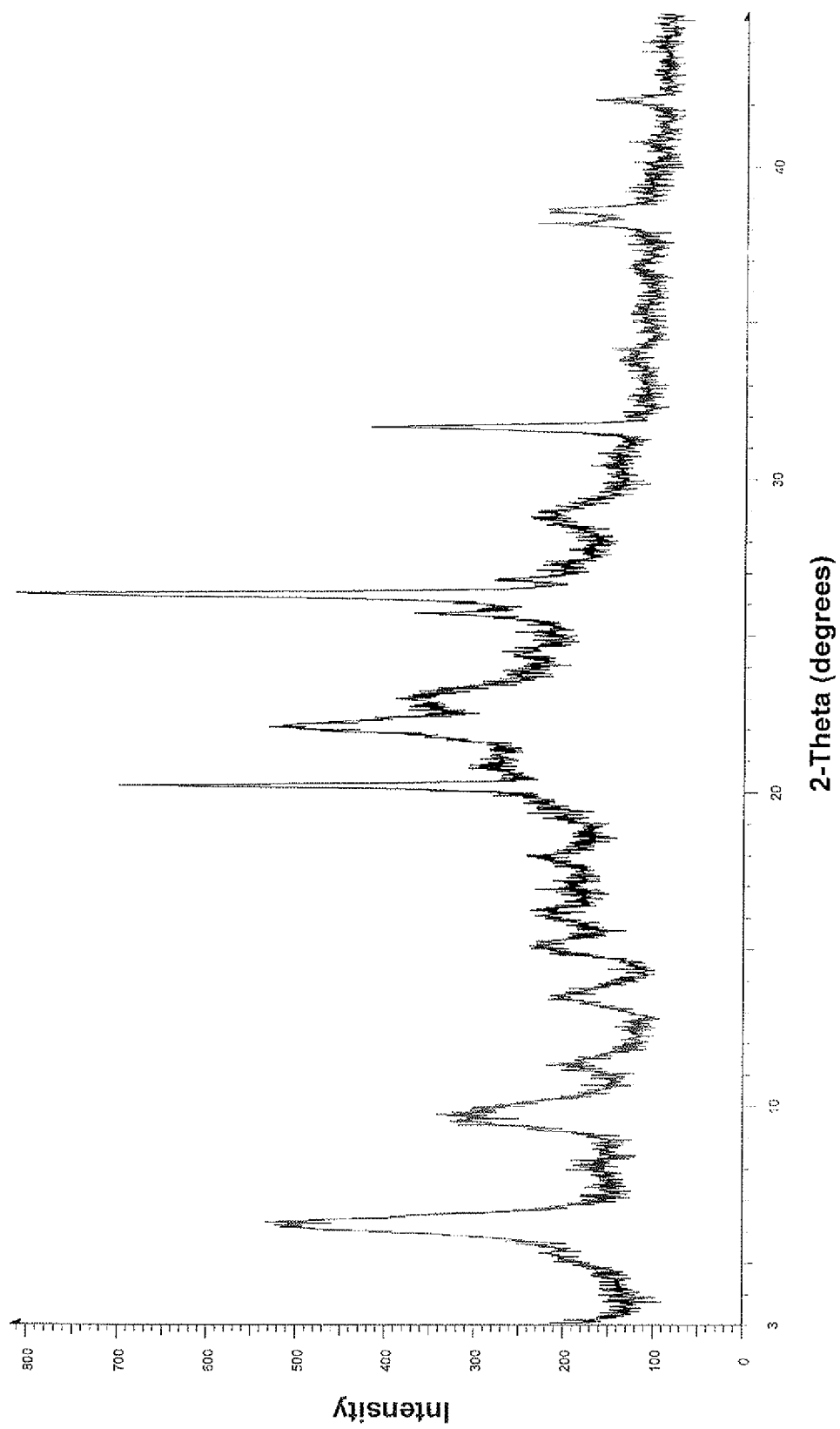
FIG. 7 is an illustration of powder X-ray diffraction ("PXRD") pattern of Ticagrelor succinate Form II prepared according to example 23.

In an embodiment, there is provided crystalline Form II of Ticagrelor succinate, having a PXRD pattern with peaks located substantially as shown in FIG. 7.

For example, there is provided a novel crystalline Form of Ticagrelor fumarate characterized by its powder X-ray diffractogram comprising peaks at 22.84, 22.45, 21.24, 20.92 and 5.22 degrees of 2θ values. A PXRD pattern with two or more peaks further selected from about 20.66, 20.09, 15.69, 15.25, 13.89, 10.89 and 9.52 degrees of 2θ values.

Figure 8:
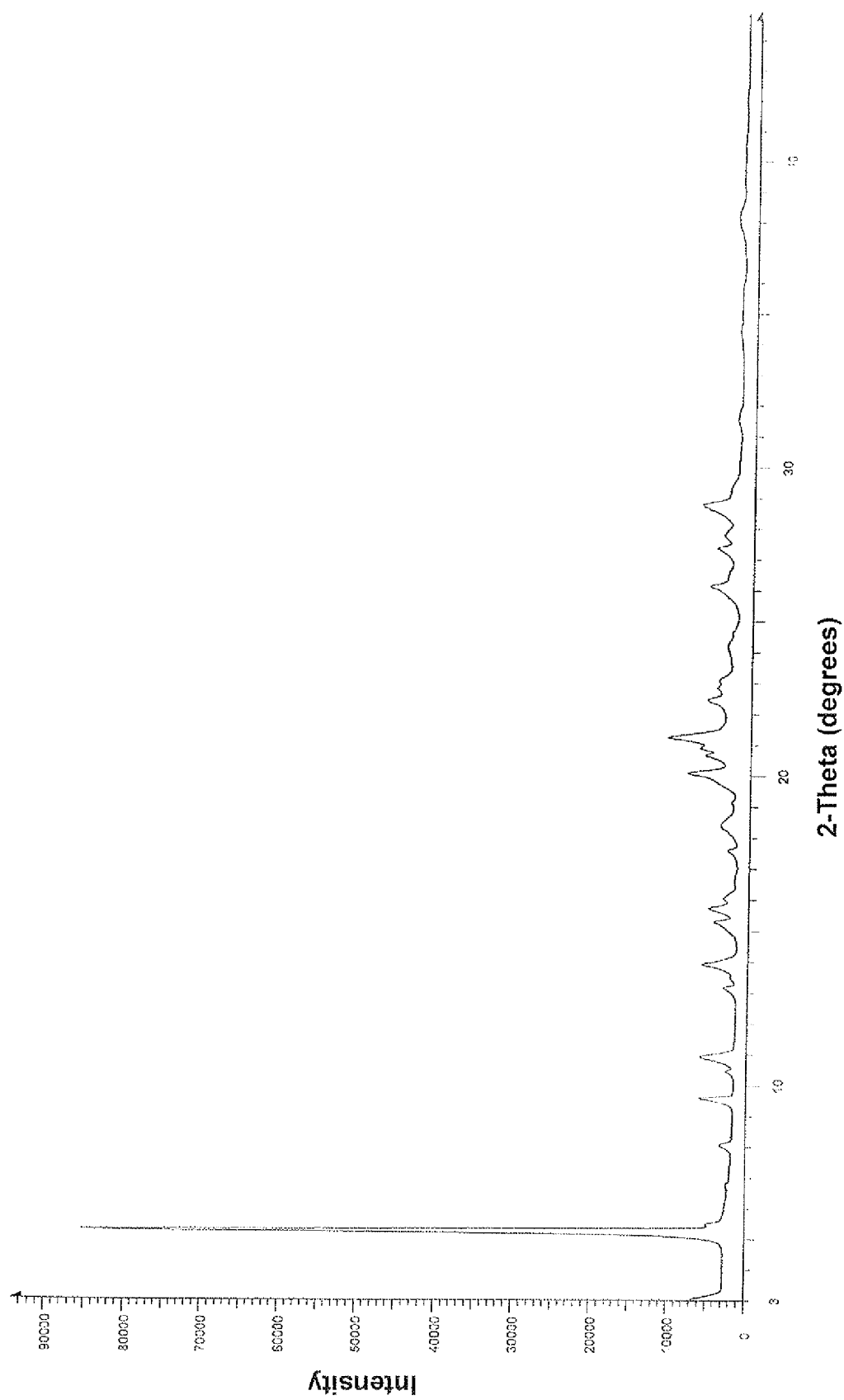
FIG. 8 is an illustration of powder X-ray diffraction ("PXRD") pattern of Ticagrelor fumarate prepared according to example 24.

In an embodiment, there is provided crystalline Form of Ticagrelor fumarate, having a PXRD pattern with peaks located substantially as shown in FIG. 8.

For example, there is provided a novel crystalline Form of Ticagrelor ID-tartrate characterized by its powder X-ray diffractogram comprising peaks at 22.47, 20.67, 20.23, 18.77, 18.25, 7.84, 7.03, 4.97 and 4.53 degrees of 2θ values. A PXRD pattern with two or more peaks further selected from about 37.24, 32.29, 29.96, 28.23, 25.12, 16.47, 16.09, 14.17 and 13.82 degrees of 2θ values.

Figure 9:
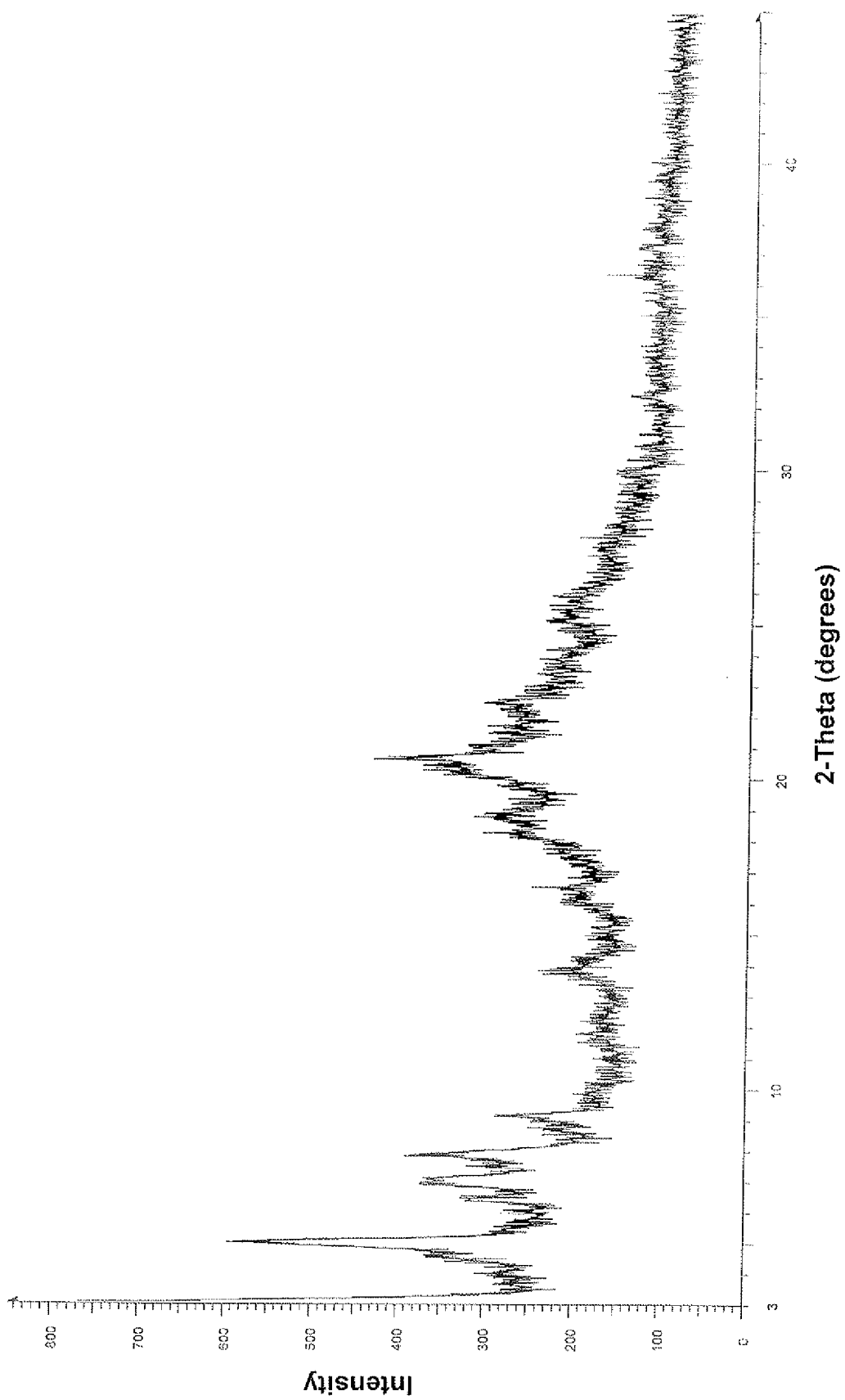
FIG. 9 is an illustration of powder X-ray diffraction ("PXRD") pattern of Ticagrelor D-tartrate prepared according to example 25.

In an embodiment, there is provided crystalline Form of Ticagrelor D-tartrate, having a PXRD pattern with peaks located substantially as shown in FIG. 9.

For example, there is provided a novel crystalline Form of Ticagrelor L-tartrate characterized by its powder X-ray diffractogram comprising peaks at 36.79, 35.91, 29.81, 25.15, 22.59, 20.80, 20.24 and 18.88 degrees of 2θ values. A PXRD pattern with two or more peaks further selected from about 36.28, 35.46, 33.52, 32.11, 29.27, 27.81, 23.36, 17.01, 11.70 and 3.66 degrees of 2θ values.

Figure 10:
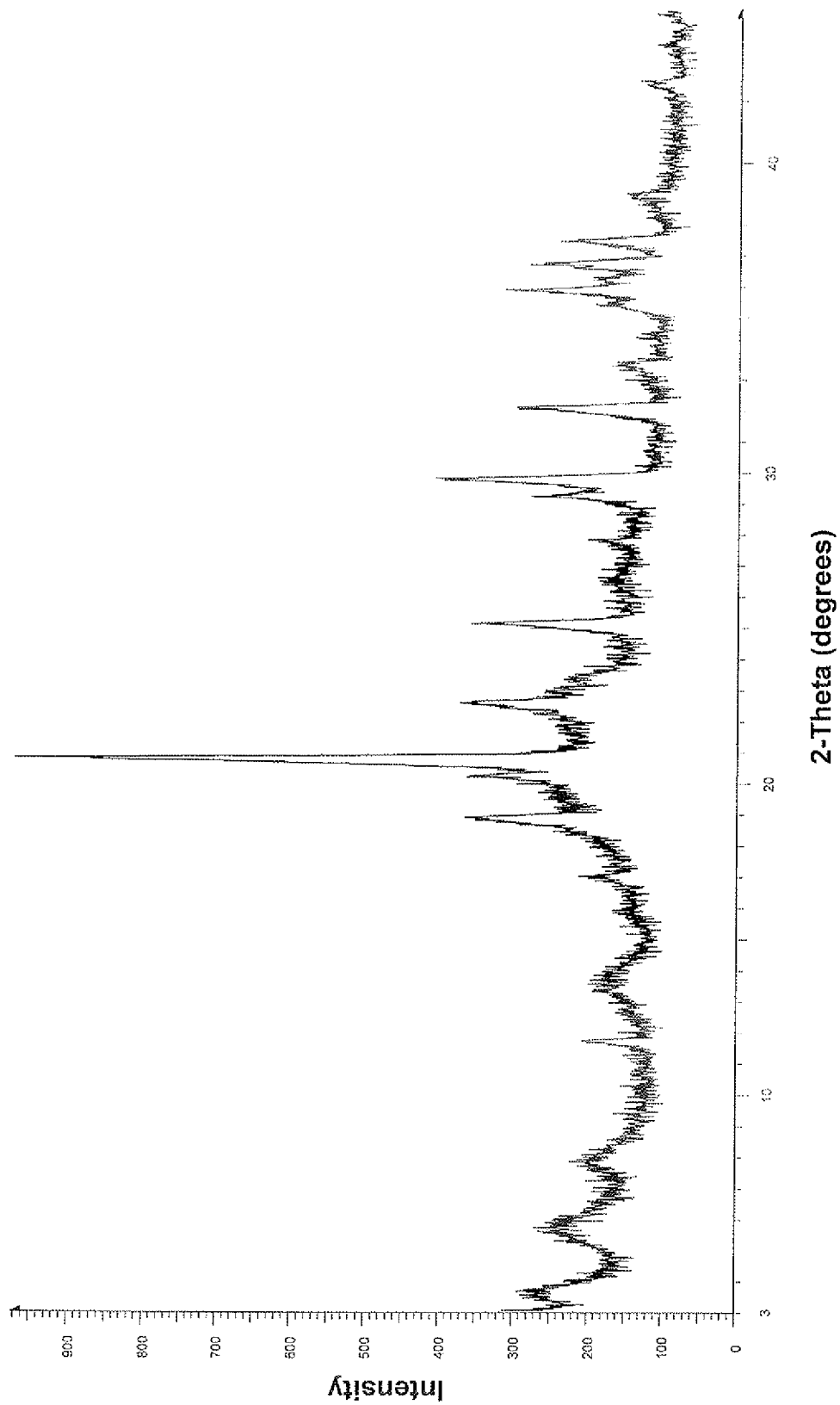
FIG. 10 is an illustration of powder X-ray diffraction ("PXRD") pattern of Ticagrelor L-tartrate prepared according to example 26.

In an embodiment, there is provided crystalline Form of Ticagrelor L-tartrate, having a PXRD pattern with peaks located substantially as shown in FIG. 10.

Figure 11:
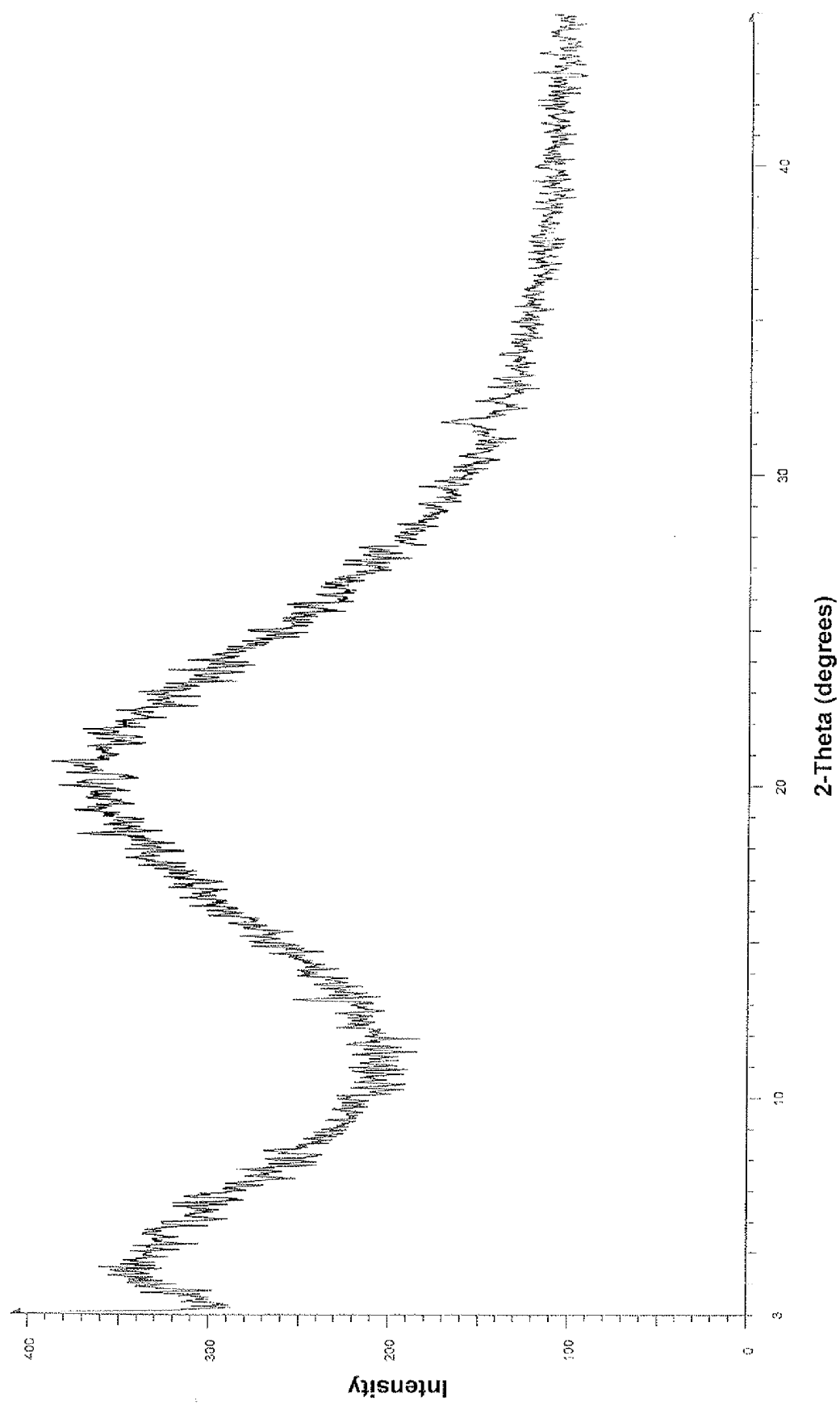
FIG. 11 is an illustration of powder X-ray diffraction ("PXRD") pattern of Ticagrelor DPTTA salt prepared according to example 27.

For example, there is provided amorphous Form of Ticagrelor DPTTA salt, having a PXRD pattern substantially as shown in FIG. 11.

For example, there is provided a crystalline Form of Ticagrelor malonate characterized by its powder X-ray diffractogram comprising peaks at 25.57, 21.39, 20.94, 18.93, 18.03, 14.32, 12.14, 9.51, 6.06 and 4.71 degrees of 2θ values. A PXRD pattern with two or more peaks further selected from about 32.42, 28.89, 28.43, 24.23, 23.33, 23.15, 22.21, 19.46, 17.52, 17.07, 13.60, 12.91, 12.73 and 8.74 degrees of 2θ values.

Figure 12:
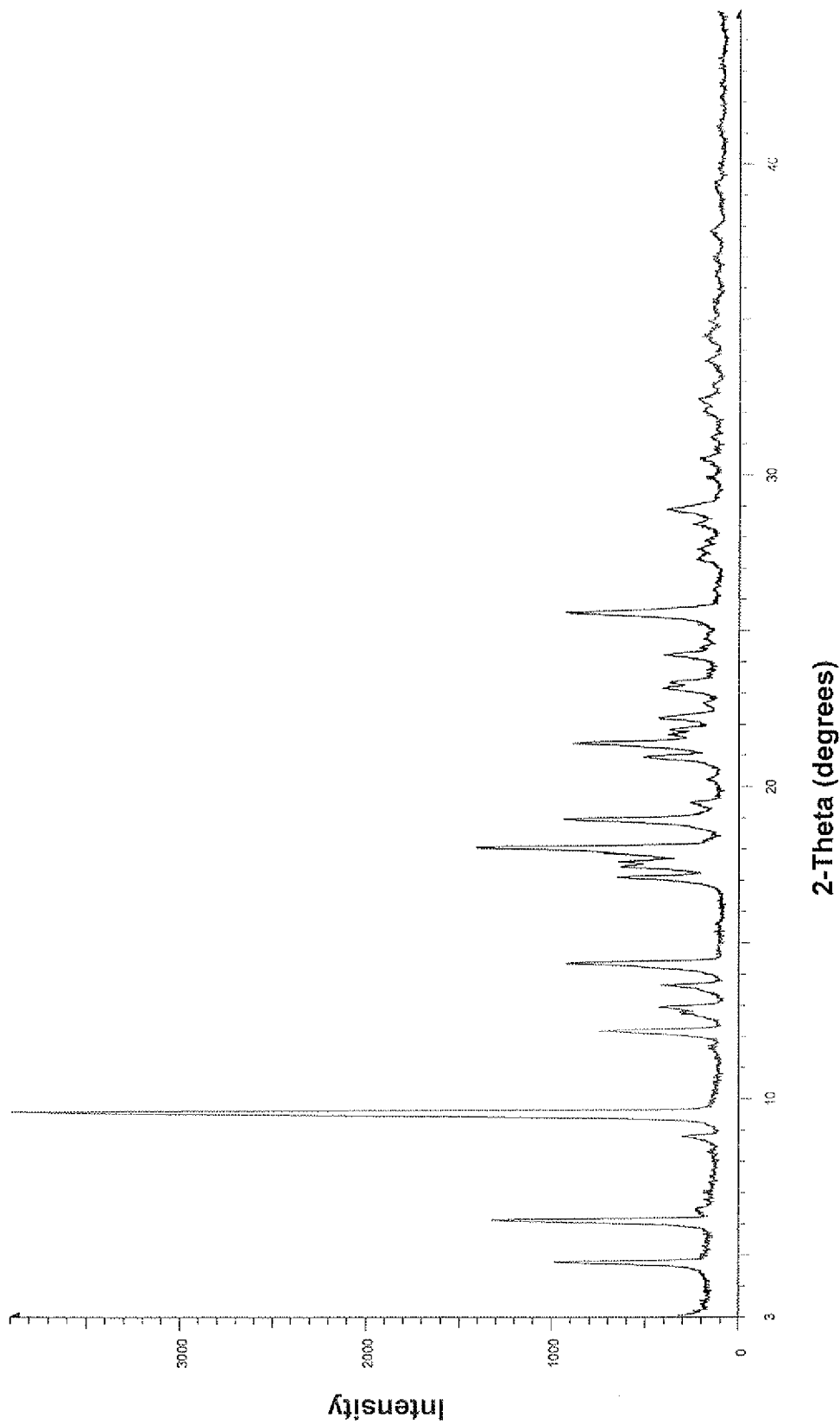
FIG. 12 is an illustration of powder X-ray diffraction ("PXRD") pattern of Ticagrelor malonate prepared according to example 28.
Figure 13:
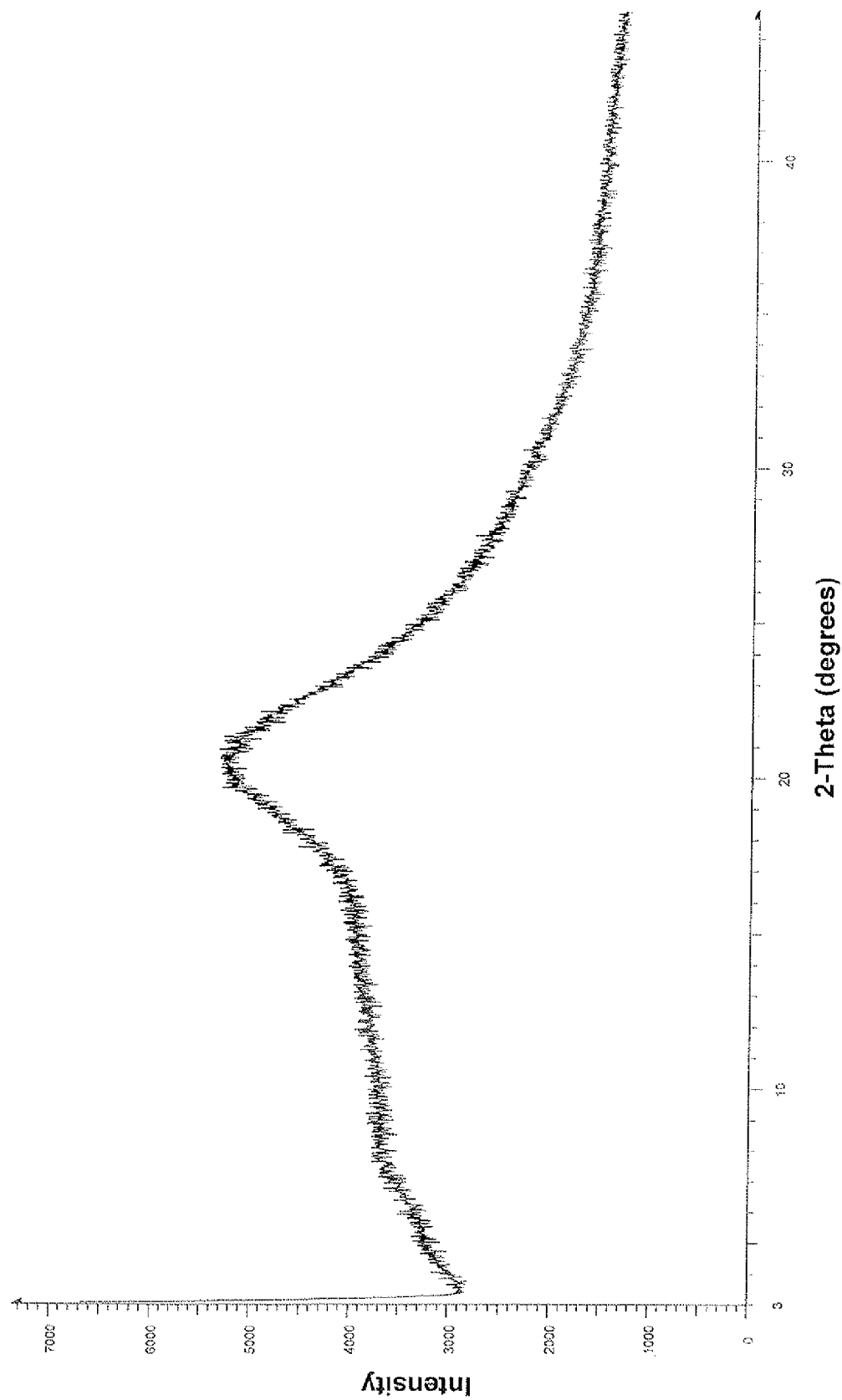
FIG. 13 is an illustration of powder X-ray diffraction ("PXRD") pattern of Ticagrelor present in solid dispersion according to example 33.

In an embodiment, there is provided crystalline Form of Ticagrelor malonate, having a PXRD pattern with peaks located substantially as shown in FIG. 12.

An aspect of the invention provides a solid dispersion comprising ticagrelor dispersed in a carrier matrix with improved properties relating to solubility, dissolution and bioavailability.

A solid dispersion is a molecular dispersion of a compound, particularly a drug substance within a carrier matrix. Formation of a molecular dispersion provides a means of reducing the particle size to nearly molecular levels (i.e. there are no particles). As the carrier dissolves, the drug is exposed to the dissolution media as fine particles that are amorphous, which can dissolve and be absorbed more rapidly than larger particles.

In general, the term "solid dispersion" refers to a system in a solid state comprising at least two components, wherein one component is dispersed throughout the other component or components. The term "amorphous solid dispersion" as used herein, refers to stable solid dispersions comprising amorphous drug substance and a carrier matrix. By "amorphous drug substance," it is meant that the amorphous solid dispersion contains drug substance in a substantially amorphous solid state form i.e. at least 80% of the drug substance in the dispersion is in an amorphous form. More preferably at least 90% and most preferably at least 95% of the drug substance in the dispersion is in amorphous form.

The solid dispersions of Ticagrelor of the present invention can be made by any of numerous methods that result in an amorphous solid dispersion of ticagrelor. Several approaches can be used for the preparation of solid dispersion which includes spray drying, fusion method, solvent evaporation, hot-melt extrusion, particle size reduction, supercritical fluid (SCF) processes, kneading, inclusion complexes, electrostatic spinning method and surface-active carriers.

Ticagrelor can be incorporated in the dispersion in amorphous or in any crystalline form. The crystalline polymorphic forms include hydrates, solvates, co-crystals etc. Moreover, Ticagrelor can be present in its free base form or in the form of any pharmaceutically acceptable salt or ester known to a person skilled in the art.

The dispersing agent is typically composed of a pharmaceutically acceptable substance that does not substantially interfere with the pharmaceutical action of ticagrelor. The phrase "pharmaceutically acceptable" is employed herein to refer to those substances which are, within the scope of sound medical judgment, suitable for use in contact with the tissues of human beings and animals without excessive toxicity, irritation, allergic response, or other problem or complication, commensurate with a reasonable benefit/risk ratio. In some embodiments, the carrier is a solid at room temperature (e.g., about 25° C.). In further embodiments, the carrier melts at a temperature between about 30 and 100° C. In further embodiments, the carrier is soluble in an organic solvent.

Non-limiting examples of suitable carriers include polymers such as celluloses (e.g., carboxymethylcelluloses, methylcelluloses, hydroxypropylcelluloses, hydroxypropylmethylcelluloses); polysaccharides, heteropolysaccharides (pectins); poloxamers; poloxamines; ethylene vinyl acetates; polyethylene glycols; dextrans; polyvinylpyrrolidones; chitosans; polyvinylalcohols; propylene glycols; polyvinylacetates; phosphatidylcholines (lecithins); miglyols; polylactic acid; polyhydroxybutyric acid; mixtures of two or more thereof, copolymers thereof, derivatives thereof, and the like. Further examples of carriers include copolymer systems such as polyethylene glycol-polylactic acid (PEG-PLA), polyethylene glycol-polyhydroxybutyric acid (PEG-PHB), polyvinylpyrrolidone-polyvinylalcohol (PVP-PVA), and derivatized copolymers such as copolymers of N-vinyl purine (or pyrimidine) derivatives and N-vinylpyrrolidone.

An enteric polymer can also be used as a carrier of the present invention. Specific examples of the enteric polymers include cellulose acetate phthalate, cellulose acetate trimellitate, cellulose acetate succinate, hydroxymethylcellulose ethyl phthalate, hydroxypropylmethylcellulose phthalate, hydroxypropylmethylcellulose acetate succinate, hydroxypropylmethyl acetate maleate, hydroxypropylmethyl trimellitate, carboxymethylethylcellulose, polyvinyl butyrate phthalate, polyvinyl alcohol acetate phthalate, methacrylic acid/ethyl acrylate copolymer, and methacrylic acid/methyl methacrylate copolymer, hydroxypropyl methylcellulose phthalate, hydroxypropylmethylcellulose acetate succinate, hydroxypropylmethyl acetate maleate and hydroxypropylmethyl trimellitate.

In an aspect of the invention, the carrier is polyvinylpyrrolidone (PVP) or a derivative thereof. PVP is a polyamide that forms complexes with a wide variety of substances and is considered to be chemically and physiologically inert. Examples of suitable PVPs include polyvinylpyrrolidones having an average molecular weight from about 10,000 to about 50,000. In some embodiments, the polyvinylpyrrolidone has an average molecular weight of about 10,000 to about 20,000. In further embodiments, the polyvinylpyrrolidone has a molecular weight of about 15,000 to about 20,000.

In an embodiment, solid dispersion of ticagrelor is prepared by dissolving Ticagrelor and the PVP in methanol to form a solution and then removing the solvent to yield an amorphous solid dispersion in the form of a powder.

In another embodiment, solid dispersion of Ticagrelor is prepared by dissolving Ticagrelor and the PVP in methanol to form a feed solution and pumping the feed solution through an atomizer into a drying chamber, and removing the solvent to yield an amorphous solid dispersion of ticagrelor in the form of a powder in the drying chamber.

In yet another embodiment, solid dispersion of Ticagrelor is prepared by dissolving Ticagrelor and PVP in methanol to form a solution, which is then sprayed onto an inert carrier substance.

The dispersing solvent can be an aqueous solvent or an organic solvent or mixture thereof. Suitable organic solvents include but are not limited to alcohols, ethers, hydrocarbons, halogenated hydrocarbons, nitriles, mixtures thereof, and the like. In some embodiments, the organic solvent is a volatile solvent such as methanol, ethanol, isopropanol, diethyl ether, pentane, hexane, benzene, dichloromethane, acetonitrile, mixtures thereof and the like. In preferred embodiments, the organic solvent is an alcohol such as methanol, ethanol, n-propanol, isopropanol, mixtures thereof and the like. In a more preferred embodiment, the organic solvent is methanol. A mixture of solvents is preferred if the drug substance and stabilizing polymer require different solvents to obtain the desired solubility.

Although the solid dispersions of the present invention are preferably prepared using conventional spray drying techniques, it will be understood that suitable solid dispersions may be formed utilizing other conventional techniques known to those skilled in the art, such as vacuum drying, fluid-bed drying, freeze-drying, rotary evaporation, drum drying, or other solvent removal process.

Another aspect of the invention involves preparation of solid dispersions of Ticagrelor by melt processing, wherein the compound and a carrier are heated to a temperature above the melting point of both the carrier and compound, which results in the formation of a fine colloidal (as opposed to molecular) dispersion of compound particles, with some solubilization of the compound in the carrier matrix. Processing of such a molten mixture often includes rapid cooling, which results in the formation of a congealed mass which must be subsequently milled to produce a powder which can be filled into capsules or made into tablets.

The amount of Ticagrelor in the solid dispersions of the present invention ranges from about 0.1% to about 90%, by weight, of the solid dispersion; or from about 10% to about 70%, by weight, of the solid dispersion; or from about 20% to about 60%, by weight, of the solid dispersion; or from about 20% to about 40%, by weight, of the solid dispersion; or about 30%, by weight, of the solid dispersion. In some aspects, the weight ratio of Ticagrelor to carrier is about 1:99 to about 99:1. In some aspects, the weight ratio of Ticagrelor to carrier is about 1:99 to about 75:25 or about 1:99 to about 60:40. In further aspects, the weight ratio of Ticagrelor to carrier is about 1:99 to about 15:85; about 1:99 to about 10:90; or about 1:99 to about 5:95. In further aspects, the weight ratio of Ticagrelor to carrier is about 25:75 to about 75:25, about 40:60 to about 60:40 or about 1:1 or about 2:1. Typically Ticagrelor and carrier medium are present in a ratio by weight with the solvent of 1:0.1 to 1:20.

The pharmaceutical dosage form according to the present invention can further comprise additional excipients and adjuvants, which are pharmaceutically acceptable and general coating materials, which are preferably applied as a coating to the pharmaceutical dosage form of the present invention. Such further excipients and adjuvants are known to the person skilled in the art.

Pharmaceutically acceptable excipients generally used in the art are combined with the isolated solid dispersion powder to form a pharmaceutical composition. Such pharmaceutically acceptable excipients may include one or more fillers; diluents, for example microcrystalline cellulose, lactose, mannitol, dibasic calcium phosphate, pregelatinized starch and the like; binders such as PVP, HPMC, HPC and the like; disintegrants, for example, sodium starch glycolate, crospovidone, croscarmellose sodium and the like; lubricants, for example, magnesium stearate, sodium stearyl fumarate and the like; sweeteners, for example, sucrose, saccharin and the like; flavoring agents, for example, peppermint, methyl salicylate, orange flavoring and the like; colorants; preservatives; buffers; and/or other excipients depending on the dosage form used.

The pharmaceutical compositions of the present invention are generally administered orally to patients, which include, but are not limited to, mammals, for example, humans, in the form of, for example, a hard or soft gelatin capsule, a tablet, a caplet, pills, granules or a suspension. The pharmaceutical dosage form can be prepared by methods known in the art, such as direct compression or wet granulation or direct compression. The compression of the blend to tablet cores can be carried out using a conventional tabletting machine or a rotary compression machine. The tablet cores may vary in shape and can be, for example, round, oval, oblong, cylindrical or any other suitable shape. The cores may also vary in size depending on the concentration of the therapeutic agent.

The pharmaceutical dosage form according to the present invention may be is coated with one or more coating materials or uncoated. The coating materials are not particularly limited and are known to the person skilled in the art.

The pharmaceutical dosage form of the present invention is usually formulated in dose units. The dose unit contains from 50 to 300 mg, advantageously from 70 to 240 mg, preferably from 90 to 180 mg of Ticagrelor or its pharmaceutically acceptable salts thereof. Such a dosage form is normally administered from 1 to 2 to 4 times daily, preferably 2 times daily.

Certain specific aspects and embodiments of the present application will be explained in greater detail with reference to the following examples, which are provided by way of illustration only and should not be construed as limiting the scope of the application in any manner.

DEFINITIONS

The following definitions are used in connection with the present application, unless the context indicates otherwise.

Polymorphs are different solids sharing the same molecular formula, yet having distinct physical properties when compared to other polymorphs of the same formula.

All percentages and ratios used herein are by weight of the total composition, unless the context indicates otherwise. All temperatures are in degrees Celsius unless specified otherwise and all measurements are made at 25° C. and atmospheric pressure unless otherwise designated. All ranges recited herein include the endpoints, including those that recite a range "between" two values. As used herein, a "room" or "ambient" temperature includes temperatures from about 15° C. to about 35° C., from about 20° C. to about 30° C., or about 25° C.

As used herein, "comprising" means the elements recited, or their equivalents in structure or function, plus any other element or elements which are not recited. The terms "having" and "including" are also to be construed as open ended unless the context suggests otherwise. Terms such as "about," "generally," "substantially," and the like are to be construed as modifying a term or value such that it is not an absolute. Such terms will be defined by the circumstances and the terms that they modify, as those terms are understood by those of skill in the art. This includes, at very least, the degree of expected experimental error, technique error, or instrument error for a given technique used to measure a value.

Where this document refers to a material, such as in this instance, salts of Ticagrelor, and the unique crystalline forms, solvates and/or optical isomers thereof by reference to patterns, spectra or other graphical data, it may do so by qualifying that they are "substantially" shown or as depicted in a Figure, or by one or more data points. By "substantially" used in such a context, it will be appreciated that patterns, spectra and other graphical data can be shifted in their positions, relative intensities and/or values due to a number of factors known to those of skill in the art. For example, in the crystallographic and powder X-ray diffraction arts, such shifts in peak positions or the relative intensities of one or more peaks can occur because of, without limitation: the equipment used, the sample preparation protocol, preferred packing and orientations, the radiation source, operator error, method and length of data collection, and the like. However, those of ordinary skill in the art should be able to compare the figures herein with a pattern generated of an unknown form of, in this case, salts of Ticagrelor, and confirm its identity as one of the forms disclosed and claimed herein. The same holds true for other techniques which may be reported herein.

In addition, where a reference is made to a figure, it is permissible to, and this document includes and contemplates, the selection of any number of data points illustrated in the figure which uniquely define that crystalline form, salt and/or optical isomer, within any associated and recited margin of error, for purposes of identification.

When a molecule or other material is identified herein as "pure", it generally means, unless specified otherwise, that the material is 99% pure or more, as determined by methods conventional in art such as high performance liquid chromatography (HPLC) or optical methods. In general, this refers to purity with regard to unwanted residual solvents, reaction byproducts, impurities, and unreacted starting materials. In the case of stereoisomers, "pure" also means 99% of one enantiomer or diastereomer, as appropriate. "Substantially" pure means, the same as "pure except that the lower limit is about 98% pure or more and likewise, "essentially" pure means the same as "pure" except that the lower limit is about 95% pure.

As used herein, the term "overnight" refers to a time interval from about 14 hours to about 24 hours, or about 14 hours to about 20 hours, for example, about 16 hours.

The "carrier" as used herein, refers to any substance or mixture of substances that acts as a dispersing medium for molecules/particles of Ticagrelor.

The term "dispersed" means random distribution of a therapeutically active substance throughout the carrier.

An "alcohol" is an organic liquid containing a carbon bound to a hydroxyl group, including, but not limited to, methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, $C_{1-6}$ alcohols, and the like.

An "ether" is an organic liquid containing an oxygen atom —O— bonded to two carbon atoms, including, but not limited to, diethyl ether, diisopropyl ether, methyl t-butyl ether, glyme, diglyme, tetrahydrofuran, 1,4-dioxane, dibutyl ether, dimethylfuran, 2-methoxyethanol, 2-ethoxyethanol, anisole, $C_{2-6}$ ethers, and the like.

A "halogenated hydrocarbon" is an organic liquid containing a carbon bound to a halogen, including, but not limited to, dichloromethane, 1,2-dichloroethane, trichloroethylene, perchloroethylene, 1,1,1-trichloroethane, 1,1,2-trichloroethane, chloroform, carbon tetrachloride, and the like.

A "ketone" is an organic liquid containing a carbonyl group —(C=O)— bonded to two other carbon atoms, including, but not limited to, acetone, ethyl methyl ketone, diethyl ketone, methyl isobutyl ketone, $C_{3-6}$ ketones, and the like.

A "hydrocarbon" is a liquid compound formed from carbon and hydrogen atoms, and may be linear, branched, cyclic, saturated, unsaturated, non-aromatic, or aromatic. Examples include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$ aliphatic hydrocarbons, petroleum ethers, benzene, toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$ aromatic hydrocarbons, and the like.

A "nitrile" is an organic liquid containing a cyano —(C≡N) bonded to another carbon atom, including, but not limited to, acetonitrile, propionitrile, $C_{2-6}$ nitriles, and the like.

A "polar aprotic solvent" has a dielectric constant greater than 15 and includes: amide-based organic solvents, such as hexamethyl phosphoramide (HMPA), hexamethyl phosphorus triamide (HMPT), and N-methylpyrrolidone, nitro-based organic solvents, such as nitromethane, nitroethane, nitropropane, and nitrobenzene; ester-based organic solvents, such as γ-butyrolactone, ethylene carbonate, propylene carbonate, butylene carbonate, dimethyl carbonate, and propiolactone; pyridine-based organic solvents, such as pyridine and picoline; and sulfone-based solvents, such as dimethylsulfone, diethylsulfone, diisopropylsulfone, 2-methylsulfolane, 3-methylsulfolane, 2,4-dimethylsulfolane, 3,4-dimethylsulfolane, 3-sulfolane, and sulfolane.

Any organic solvents may be used alone, or any two or more may be used in combination, or one or more may be used in combination with water in desired ratios.

Acid addition salts are typically pharmaceutically acceptable, non-toxic addition salts with "suitable acids," including, but not limited to: inorganic acids such as hydrohalic acids (for example, hydrofluoric, hydrochloric, hydrobromic, and hydroiodic acids) or other inorganic acids (for example, nitric, perchloric, sulfuric, and phosphoric acids); organic acids, such as organic carboxylic acids (for example, xinafoic, oxalic, propionic, butyric, glycolic, lactic, mandelic, citric, acetic, benzoic, 2- or 4-methoxybenzoic, 2- or 4-hydroxybenzoic, 2- or 4-chlorobenzoic, salicylic, succinic, malic, hydroxysuccinic, tartaric, fumaric, maleic, hydroxymaleic, oleic, and glutaric acids), organic sulfonic acids (for example, methanesulfonic, trifluoromethanesulfonic, ethanesulfonic, 2-hydroxyethanesulphonic, benzenesulfonic, toluene-p-sulfonic, naphthalene-2-sulphonic, and camphorsulfonic acids), and amino acids (for example, ornithinic, glutamic, and aspartic acids).

Certain specific aspects and embodiments of the present application will be explained in greater detail with reference to the following examples, which are provided only for purposes of illustration and should not be construed as limiting the scope of the disclosure in any manner.

As used herein, the terms "salt(s) of Ticagrelor," "Ticagrelor salt(s)" and other similar phrases encompass crystalline and amorphous forms, solvates, hydrates, stereoisomers, both individual and in mixtures thereof, racemates, enantiomers, or the like.

EXAMPLES

Example 1

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 4,6-dichloro-2-(propylthio)pyrimidin-5-amine (5 g), 2-(((3aR,4S,6R,6aS)-6-amino-2,2-dimethyltetrahydro-3aH-cyclopenta[d][1,3]dioxol-4-yl)oxy)ethanol L-tartaric acid salt (8.5 g), water (30 mL) and sodium bicarbonate (10.5 g). The mixture was heated to about 90-100° C. and maintained at the same temperature for about 8-9 hours and completion of the reaction was monitored by TLC. After completion of reaction the mixture was cooled to 25-30° C. followed by addition of water (100 mL) and toluene (50 mL). The mixture was stirred for about 20 minutes and layers were separated. The organic layer was washed with water (50 mL). The organic layer was separated and subjected to complete distillation under vacuum at 60-65° C. followed by cooling to room temperature and subsequent addition of n-heptane (75 mL). The mixture was stirred for about 2 hours followed by isolation of solid by filtration and washing with n-heptane (10 mL). The solid isolated was subjected to drying under vacuum at 60-65° C. for 1 hour to afford the title compound in about 80% yield having HPLC purity of about 99.03%.

Example 2

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 2-(((3aR,4S,6R,6aS)-6-amino-2,2-dimethyltetrahydro-3aH-cyclopenta[d][1,3]dioxol-4-yl)oxy)ethanol L-tartaric acid salt (17 g), sodium bicarbonate (21.2 g), 4,6-dichloro-2-(propylthio)pyrimidin-5-amine (10 g) and isoamyl alcohol (30 mL). The mixture was heated to about 100-110° C. and maintained at the same temperature for about 10-12 hours and completion of the reaction was monitored by TLC. After completion of reaction the mixture was cooled to room temperature then filtered and the bed was washed with isoamyl alcohol (10 mL). The filtrate was subjected to complete distillation under vacuum at about 65-70° C. to afford the crude. Then water (100 mL) and toluene (100 mL) were charged. The mixture was stirred for about 20 minutes and layers were separated. The organic layer was separated and washed with water (100 mL). The organic layer was separated and subjected to complete distillation under vacuum at 60-65° C. followed by cooling to room temperature and subsequent addition of n-heptane (150 mL). The mixture was stirred for about 4-5 hours followed by isolation of solid by filtration and washing with n-heptane (20 mL). The solid isolated was subjected to drying under vacuum at 50-55° C. to afford the title compound in about 82% yield having HPLC purity of about 99%.

Example 3

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 4,6-dichloro-2-(propylthio)pyrimidin-5-amine (3 g), 2-(((3aR,4S,6R,6aS)-6-amino-2,2-dimethyltetrahydro-3aH-cyclopenta[d][1,3]dioxol-4-yl)oxy)ethanol L-tartaric acid salt (5.1 g), dimethyl sulfoxide (30 mL) and triethyl amine (7.05 g). The mixture was heated to about 60-65° C. and maintained at the same temperature for about 24 hours and completion of the reaction was monitored by TLC. After completion of reaction the mixture was cooled to 25-30° C. followed by addition of water (30 mL) and toluene (30 mL). The mixture was stirred for about 10 minutes and layers were separated. The organic layer was sequentially washed with 5% aqueous sodium carbonate solution (30 mL), 5% aqueous acetic acid solution (30 mL) and sodium chloride solution (30 mL). The organic layer was separated and subjected to complete distillation under vacuum at 55-60° C. followed by cooling to room temperature and subsequent addition of n-hexane (55 mL). The mixture was stirred for about 2-3 hours followed by isolation of solid by filtration and washing with n-hexane (10 mL). The solid isolated was subjected to drying under vacuum at 55-60° C. for 90 minutes to afford the title compound in about 60% yield having HPLC purity of about 96%.

Example 4

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 4,6-dichloro-2-(propylthio)pyrimidin-5-amine (50 g), 2-(((3aR,4S,6R,6aS)-6-amino-2,2-dimethyltetrahydro-3aH-cyclopenta[d][1,3]dioxol-4-yl)oxy)ethanol L-tartaric acid salt (84.83 g), dimethyl sulfoxide (500 mL) and triethyl amine (127.5 g). The mixture was heated to about 95-105° C. and maintained at the same temperature for about 10-12 hours and completion of the reaction was monitored by TLC. After completion of reaction the mixture was cooled to 25-30° C. followed by addition of water (1000 mL) and toluene (600 mL). The mixture was stirred for about 10 minutes and layers were separated. The organic layer was sequentially washed with 20% aqueous sodium carbonate solution (1000 mL), 20% aqueous acetic acid solution (1000 mL) and water (700 mL). The organic layer was separated and subjected to complete distillation under vacuum at 60-65° C. followed by cooling to room temperature and subsequent addition of n-hexane (800 mL). The mixture was stirred for about 9 hours at room temperature followed by isolation of solid by filtration and washing with n-hexane (100 mL). The solid isolated was subjected to drying under vacuum at 55-60° C. for about 5 hours to afford the title compound in about 84% yield having HPLC purity of about 98%.

Example 5

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 4,6-dichloro-2-(propylthio)pyrimidin-5-amine (3 g), 2-(((3aR,4S,6R,6aS)-6-amino-2,2-dimethyltetrahydro-3aH-cyclopenta[d][1,3]dioxol-4-yl)oxy)ethanol L-tartaric acid salt (5.1 g), dimethyl sulfoxide (30 mL) and sodium bicarbonate (6.3 g). The mixture was heated to about 60-65° C. and maintained at the same temperature for about 10 hours and completion of the reaction was monitored by TLC. After completion of reaction the mixture was cooled to 25-30° C. followed by addition of water (30 mL) and toluene (30 mL). The mixture was stirred for about 10 minutes and layers were separated. The organic layer was with water (30 mL). The organic layer was separated and subjected to complete distillation under vacuum at 55-60° C. followed by cooling to room temperature and subsequent addition of n-hexane (45 mL). The mixture was stirred for about 3 hours at room temperature followed by isolation of solid by filtration and washing with n-hexane (15 mL). The solid isolated was subjected to drying under vacuum at 55-60° C. for about 4 hours to afford the title compound in about 78% yield having HPLC purity of about 98%.

Example 6

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 4,6-dichloro-2-(propylthio)pyrimidin-5-amine (3 g), 2-(((3aR,4S,6R,6aS)-6-amino-2,2-dimethyltetrahydro-3aH-cyclopenta[d][1,3]dioxol-4-yl)oxy)ethanol L-tartaric acid salt (5.1 g), dimethyl sulfoxide (30 mL) and triethyl amine (7.65 g). The mixture was heated to about 130-140° C. and maintained at the same temperature for about 7 hours and completion of the reaction was monitored by TLC. After completion of reaction the mixture was cooled to 25-30° C. followed by addition of water (30 mL) and toluene (30 mL). The mixture was stirred for about 10-15 minutes and layers were separated. The organic layer was sequentially washed with 5% aqueous sodium carbonate solution (30 mL), 5% aqueous acetic acid solution (30 mL) and sodium chloride solution (30 mL). The organic layer was separated and subjected to complete distillation under vacuum at 55-60° C. followed by cooling to room temperature and subsequent addition of n-hexane (45 mL). The mixture was stirred for about 11 hours at room temperature followed by isolation of solid by filtration and washing with n-hexane (10 mL). The solid isolated was subjected to drying under vacuum at 55-60° C. for about 90 minutes to afford the title compound in about 65% yield.

Example 7

Preparation of (1S,2S,3R,5S)-3-(7-Chloro-5-(Propylthio)-3H-[1,2,3]Triazolo[4,5-d]Pyrimidin-3-Yl)-5-(2-Hydroxyethoxy)Cyclopentane-1,2-Diol A flask was charged with water (20 mL) and concentrated hydrochloric acid (35%, 1.5 mL). To this, 2-(((3aR,4S,6R,6aS)-6-((5-amino-6-chloro-2-(propylthio)pyrimidin-4-yl)amino)-2,2-dimethyltetrahydro-3aH-cyclopenta[d][1,3]dioxol-4-yl)oxy)ethanol (5 g) was added and the mixture was stirred for clear solution. To this mixture, aqueous sodium nitrite solution (0.86 g in 5 mL) was slowly added at room temperature over a period of 15 minutes and mixture was stirred for about 30 minutes and completion of reaction was monitored by TLC. The solid obtained is isolated by filtration and washed with water (5 mL) and dried under vacuum to afford the title compound in about 80% yield.

Example 8

Preparation of Ticagrelor (1R,2S)-2-(3,4-difluorophenyl)cyclopropanamine mandelate (1.8 g) and ethyl acetate (20 mL) were charged in a flask. The mixture was stirred at 15-20° C. for 10 minutes followed by addition of 20% aqueous sodium hydroxide solution (25 mL). The mixture was stirred and then the layers were separated. The organic layer was taken in another flak and to it diisopropyl ethylamine (1.5 mL) and (1S,2S,3R,5S)-3-(7-chloro-5-(propylthio)-3H-[1,2,3]triazolo[4,5-d]pyrimidin-3-yl)-5-(2-hydroxyethoxyl)cyclopentane-1,2-diol were added. The mixture was stirred at room temperature for 1 hour and completion of the reaction was monitored by TLC. To the mixture water (5 mL) was added and the layers were separated. The organic layer was washed with 2% aqueous hydrochloric acid solution (10 mL) followed by complete distillation of organic solvent under vacuum. To the mass obtained ethyl acetate (10 mL) was added and then completely distilled under vacuum followed by cooling of mass to room temperature. Then ethyl acetate (10 mL) and n-hexane (50 mL) were added to the mass and mixture was stirred. The solid obtained was isolated by filtration and washed with n-hexane (5 mL) followed by drying under vacuum to afford the title compound in about 67% yield.

Example 9

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 4,6-dichloro-2-(propylthio)pyrimidin-5-amine (5 g), 2-(((3aR,4S,6R,6aS)-6-amino-2,2-dimethyltetrahydro-3aH-cyclopenta[d][1,3]dioxol-4-yl)oxy)ethanol L-tartaric acid salt (8.5 g), water (15 mL) and sodium bicarbonate (10.6 g). The mixture was heated to about 100° C. and maintained at the same temperature for about 20 hours and completion of the reaction was monitored by TLC. After completion of reaction the mixture was cooled to 30° C. followed by addition of water (50 mL) and ethyl acetate (25 mL). The mixture was stirred for about 10 minutes and layers were separated. The aqueous layer was extracted with ethyl acetate (25 mL). Total organic layer was washed with water (50 mL). The organic layer was subjected to complete distillation under vacuum at 55° C. followed by addition of ethyl acetate (5 mL). The mixture was stirred for 20 minutes followed by addition of n-hexane (75 mL). The mixture was further stirred at room temperature for solid separation followed by isolation of solid by filtration and washing with n-hexane (10 mL). The solid isolated was subjected to drying under vacuum at 60° C. for 3 hours to afford the title compound in about 91% yield having HPLC purity of about 99.18%.

Example 10

Preparation of 2-(((3aR,4S,6R,6aS)-6-((5-Amino-6-Chloro-2-(Propylthio)Pyrimidin-4-Yl)Amino)-2,2-Dimethyltetrahydro-3aH-Cyclopenta[d][1,3]Dioxol-4-Yl)Oxy)Ethanol (Formula IV)

A flask was charged with 4,6-dichloro-2-(propylthio)pyrimidin-5-amine (25 g), 2-(((3aR,4S,6R,6aS)-6-amino-2,2-dimethyltetrahydro-3aH-cyclopenta[d][1,3]dioxol-4-yl)oxy)ethanol L-tartaric acid salt (42.5 g), water (75 mL) and sodium bicarbonate (53 g). The mixture was heated to about 100° C. and maintained at the same temperature for about 14 hours and completion of the reaction was monitored by TLC. After completion of reaction, the mixture was cooled to 60° C. followed by addition of ethyl acetate (25 mL), water (175 mL) and n-hexane (375 mL). The mixture was stirred for about 7 hours. The solid obtained was isolated by filtration and washed with water (50 mL). The wet compound and water (500 mL) were charged into round bottom flask and stirred for overnight. The solid was isolated by filtration and washed with water (50 mL) and was subjected to drying under vacuum at 60° C. for 9 hours to afford the title compound in about 95% yield having HPLC purity of about 98.5%.

Example 11

Preparation of 2-(((3aR,4S,6R,6aS)-6-(7-Chloro-5-(Propylthio)-3H-[1,2,3]Triazolo[4,5-d]Pyrimidin-3-Yl)-2,2-Dimethyltetrahydro-4H-Cyclopenta[d][1,3]Dioxol-4-Yl)Oxy)Ethan-1-Ol (Formula V)

A flask was charged with 2-(((3aR,4S,6R,6aS)-6-((5-amino-6-chloro-2-(propylthio)pyrimidin-4-yl)amino)-2,2-dimethyltetrahydro-4H-cyclopenta[d][1,3]dioxol-4-yl)oxy)ethan-1-ol (50 g), acetic acid (265 mL) and water (50 mL). The mixture was stirred and cooled to 0-5° C. followed by addition of aqueous sodium nitrite solution (8.65 g in 50 mL) over a period of about 1 hour. The mixture was stirred at the same temperature for about 2 hours followed by addition of ethyl acetate (250 mL) and water (250 mL). The mixture was further stirred at room temperature for about 45 minutes at which point water (250 mL) was added. The mixture was stirred and layers were separated, aqueous layer was extracted with ethyl acetate (250 mL). Total organic layer was separated and washed with aqueous potassium carbonate solution (20%, 2×250 mL). The organic layer (~500 mL) was used for subsequent step.

Example 12

Preparation of 2-(((3aR,4S,6R,6aS)-6-(7-(((1R,2S)-2-(3,4-Difluorophenyl)Cyclopropyl)Amino)-5-(Propylthio)-3H-[1,2,3]Triazolo[4,5-d]Pyrimidin-3-Yl)-2,2-Dimethyltetrahydro-4H-Cyclopenta[d][1,3]Dioxol-4-Yl)Oxy)Ethan-1-Ol (Formula VI)

A flask was charged with (1R,2S)-2-(3,4-difluorophenyl)cyclopropanamine mandelate (36.2 g) and ethyl acetate (50 mL) followed by addition of diisopropyl ethylamine (69 g). The mixture was stirred for about 25 minutes at room temperature followed by addition of organic layer (500 mL) from previous example 11 over a period of 30 minutes at the same temperature. The mixture was stirred for about 90 minutes at room temperature for completion of reaction as verified by TLC. After completion of reaction, water was charged to the mixture and layers were separated. The organic layer was washed with 2% aqueous hydrochloric acid solution (2×250 mL) followed by 20% sodium chloride solution (250 mL). The organic layer was subjected to distillation under vacuum at 55° C. to afford the title compound in about 97% yield.

Example 13

Preparation of 2-Chloro-1-(3,4-Difluorophenyl)Ethanone (Formula VIII)

1,2-Difluorobenzene (150 g) and aluminium chloride (156 g) were charged in a round bottom flask. The reaction mixture is heated to about 60° C. followed by slow addition of chloroacetyl chloride (105 mL) over a period of 1 hour at the same temperature. The reaction mixture was stirred for another 3 hours followed by cooling to about 10° C. The reaction mass was poured into precooled water (1500 mL) followed by addition of hydrochloric acid (36%, 225 mL) at the same temperature and stirring. To this mixture ethyl acetate (750 mL) was charged and layers were separated. The aqueous layer is extracted with ethyl acetate (750 mL). The organic layers were combined and washed with water (750 mL) followed by complete evaporation of organic layer under vacuum at 50-55° C. The residue obtained is cooled to 25-35° C. followed by purification with column chromatography using 0-5% ethyl acetate in petroleum ether to afford the title compound in about 70% yield having HPLC purity of 99.51%.

Example 14

Preparation of (S)-2-Chloro-1-(3,4-Difluorophenyl) Ethanol (Formula IXA)

Trimethoxy borane (2.0 g) was added at room temperature to a stirred solution of (S)-diphenylprolinol (3.5 g) in toluene (100 mL). After stirring this mixture for 90 minutes at about 65-75° C., borane dimethylsulfide (2M THF solution, 105 mL) was added over a period of 50 minutes maintaining the temperature between 65 and 75° C. This mixture was stirred for another 90 minutes at 75° C., then a solution of 2-chloro-1-(3,4-difluorophenyl)ethanone (50.0 g) in toluene (150 mL) was dosed over a period of 25 minutes maintaining the temperature between 65 and 75° C. After the completion of the addition the reaction mixture was stirred for another 100 minutes at 75° C. at which point the completion of reaction was monitored by TLC. Then mixture was cooled to 0-5° C. and methanol (50 mL) was added over a period of 30 minutes controlling the gas formation and the temperature to a maximum of 5° C. After the addition is complete, the obtained solution was subjected to distillation under reduced pressure at below 60° C., followed by sequential addition of 10% aqueous acetic acid solution (250 mL) and toluene (500 mL) to the residue. The layers were separated and obtained water layer was back extracted with toluene (250 mL). Both organic layers were combined and washed with water (500 mL). The resulting organic layer was subjected to complete distillation under vacuum to afford the title compound in 94.2% yield having chiral HPLC purity of 99.62%.

Example 15

Preparation of (S)-2-(3,4-Difluorophenyl)Oxirane (Formula Xa)

To a mixture of 1S-2-chloro-1-(3,4-difluorophenyl)-1-ethanol (45 g) in toluene (225 mL), aqueous solution of sodium hydroxide (10.2 g in 225 mL of water) was added. The mixture was heated to 40-45° C. under stirring and maintained at same temperature for 1-2 hours till the completion of reaction as monitored by TLC followed by cooling of the mixture to 25-30° C. and subsequent addition of water (225 mL). The organic layer was separated and aqueous layer was extracted with toluene (225 mL). Both organic layers were combined and washed with water (225 mL), then organic layer was subjected to complete distillation under vacuum at below 60-65° C. to afford the title compound in ~84% yield having 99.27% chiral purity.

Example 16

Preparation of (1R,2R)-2-(3,4-Difluorophenyl)Cyclopropanecarbonitrile (Formula XIIa)

Potassium t-butoxide (21.5 g) and toluene (150 mL) were charged into a reaction vessel. Diethyl cyanomethylphosphonate (34.8 g) was added to the mixture with stirring and mixture was heated to 70-80° C. Then a mixture of (2S)-2-

(3,4-difluorophenyl) oxirane (29 g) in toluene (150 mL) was slowly added to above reaction mass at 75-80° C. over a period of 30 minutes and the mixture was maintained for 11-12 hours for completion of reaction as monitored by TLC. After completion of reaction, mixture was cooled to 25-30° C. and water (300 mL) was added, the layers were separated. The aqueous layer was back extracted with toluene (150 mL). The organic layers were combined and washed with water (300 mL). The combined organic layer was subjected to complete distillation under vacuum at below 55-60° C. to afford the compound which was purified by column chromatography to afford the title compound of about 97% HPLC purity.

Example 17

Preparation of (1R,2R)-2-(3,4-Difluorophenyl)Cyclopropane Carboxylic Acid (Formula XIIIa)

(1R,2R)-2-(3,4-difluorophenyl)cyclopropanecarbonitrile (5 g), ethanol (25 mL) were charged to a round bottom flask followed by addition of caustic lye (10 mL). The reaction mixture was heated to 80-85° C. and maintained at the same temperature for 2-3 hours till the completion of reaction as monitored by TLC. The reaction mixture was cooled to 25-30° C. and then water (15 mL) was added to the mixture. The pH of the mixture was adjusted to 1-2 with conc. hydrochloric acid (15 mL) followed by addition of ethyl acetate (25 mL). The layers were separated and aqueous layer was extracted with ethyl acetate (25 mL). The organic layers were combined and charged with water (15 mL) and caustic lye (10 mL). After stirring, the organic layer was separated and pH of the aqueous layer was adjusted to 1-2 with conc. hydrochloric acid (10 mL). To this ethyl acetate (25 mL) and water (15 mL) were added and stirred for 10-15 minutes. The layers were separated and the aqueous layer was extracted with ethyl acetate (25 mL). The organic layers were combined and washed with water (2×15 mL) followed by complete distillation of solvent from organic layer under vacuum at 50-55° C. to afford the title compound in about 94.3% yield having HPLC purity of about 99%.

Example 18

Preparation of Trans-(1R,2S)-2-(3,4-Difluorophenyl) Cyclopropanamine L-Tartrate (Formula VII'a)

(1R,2R)-2-(3,4-difluorophenyl)cyclopropanecarboxylic acid (2.5 g) and toluene (15 mL) were charged into a round bottomed flask followed by addition of pyridine (50 mg) and thionyl chloride (1 mL). The mixture was maintained at 25-35° C. for 1-2 hours till the completion of reaction as monitored by TLC. The solvent from the mixture was subjected to distillation under vacuum at 55-60° C. to afford the residue which was taken up in toluene (10 mL). In a separate flask, sodium azide (1 g), tetrabutyl ammonium bromide (0.04 g), sodium carbonate (0.8 g) and water (5 mL) were charged and mixture was cooled to 5° C. To this mixture, above solution of acid chloride in toluene was slowly added at 0-5° C. over a period of 40 minutes and the reaction mixture was maintained at same temperature for 2-3 hours followed by addition of water (3 mL). The layers were separated and organic layer was washed with water (2.5 mL) and 20% sodium chloride solution (3 mL). The organic layer was separated and kept under cold condition. In a separate flask toluene (5 mL) was taken and heated to 100-105° C. followed by slow addition of above cold toluene layer from previous step at 100° C. over a period of 20 minutes. The mixture was maintained at 100-105° C. for 60-90 minutes and then the mixture was cooled to 25-35° C. This mixture was slowly added to conc. hydrochloric acid (14 mL) at 80-85° C. over a period of 30 minutes and further maintained at 80-85° C. for 60-90 minutes followed by addition of water (25 mL). The mixture was then cooled to 25-30° C. and layers were separated. The aqueous layer was basified to pH 10-12 with 20% sodium hydroxide solution (22 mL) followed by extraction of aqueous layer with ethyl acetate (2×20 mL). The ethyl acetate layer was washed with water (20 mL) and organic layer was subjected to distillation at 50-55° C. The mixture was cooled to 25-30° C. and ethanol (15 mL) was charged followed by addition of L-tartaric acid (1.3 g) and the mixture was maintained for 1-2 hours. The solid obtained was filtered under vacuum and washed with ethanol (5 mL) and dried under vacuum at below 50-55° C. to afford the title compound in about 52% yield having chiral HPLC purity of 99.40%.

Example 19

Preparation of Form I of Ticagrelor Hydrochloride

Ticagrelor (0.5 g) and ethyl acetate (15 mL) were charged into a round bottom flask and the mixture was stirred at about 25-30° C. for about 15 minutes for clear solution. Then aqueous hydrochloric acid (0.12 mL, 35%) was added to the above reaction mixture at 25-35° C. and stirred for solid separation for about 2 hours. The solid was filtered, washed with ethyl acetate (5 mL) and dried to afford the title compound in about 75% yield having chiral HPLC purity of 99.55%.

Example 20

Preparation of Amorphous Form of Ticagrelor Hydrochloride

Ticagrelor (1 g) and ethyl acetate (30 mL) were charged into a round bottom flask and stirred at about 30° C. for about 15 minutes. The reaction mixture was filtered through hyflow bed followed by washing with ethyl acetate (5 mL). Then aqueous hydrochloric acid (0.24 mL, 35%) was added to the above filtrate at about 30° C. and mixture was stirred for about 1 hour. The reaction mixture was concentrated up to 20% of its initial volume at 40° C. under reduced pressure. Then petroleum ether (70 mL) was added to the reaction mixture at about 30° C. and mixture was stirred for about 90 minutes for solid separation. The solid was isolated by filtration under nitrogen atmosphere and dried at below 50° C. to afford the title compound in about 47.2% yield.

Example 21

Preparation of Ticagrelor Hydrobromide

Ticagrelor (1 g) and ethyl acetate (30 mL) were charged into a round bottom flask and stirred at about 30° C. for 15 minutes. The reaction mixture was filtered through hyflow bed followed by washing of the bed with ethyl acetate (5 mL). Then aqueous hydrobromic acid (0.37 mL, 48%) was added to the above filtrate at same temperature and stirred for about 1 hour. The reaction mixture was concentrated up to 20% of its initial volume at 45° C. under reduced pressure. Then petroleum ether (70 mL) was added to the reaction mixture at 30° C. and stirred for about 90 minutes for solid separation.

The solid obtained was isolated by filtration and dried at below 50° C. to afford the title compound in about 69.6% yield.

Example 22

Preparation of Form I of Ticagrelor Succinate

Ticagrelor (0.5 g) and acetone (10 mL) were charged into a round bottom flask and the mixture was stirred at about 25-30° C. for about 15 minutes for clear solution. Then succinic acid (0.12 g) was added to the above reaction mixture at 25-35° C. and stirred overnight. To the clear solution, n-hexane (50 mL) was added and stirred for about 90 minutes for solid separation. The solid was isolated by filtration, washed with n-hexane (5 mL) and dried to afford the title compound in about 81% yield having chiral HPLC purity of about 99%.

Example 23

Preparation of Form II of Ticagrelor Succinate

Ticagrelor (2 g) and acetone (40 mL) were charged into a round bottom flask and stirred at about 30° C. for about 15 minutes. The reaction mixture was filtered through hyflow bed followed by washing of the bed with acetone (5 mL). Then succinic acid (0.5 g) was added to the above filtrate at about 30° C. and mixture was stirred for 1 hour. The reaction mixture was concentrated up to 20% of its initial volume at 45° C. under reduced pressure. Then n-hexane (45 mL) was added to the reaction mixture at about 30° C. and mixture was stirred for about 2-3 hours for solid separation. The solid was isolated by filtration and dried at below 50° C. to afford the title compound in about 32.65% yield.

Example 24

Preparation of Ticagrelor Fumarate

Ticagrelor (0.5 g) and acetone (13 mL) were charged into a round bottom flask and the mixture was stirred at about 25-30° C. for about 15 minutes for clear solution. Then fumaric acid (0.12 g) was added to the above reaction mixture at 25-35° C. and mixture was stirred for 4-5 hours. To the clear solution, n-hexane (50 mL) was added and stirred for about 90 minutes for solid separation. The solid was filtered, washed with n-hexane (5 mL) and dried to afford the title compound in about 65% yield having chiral HPLC purity of about 99.8%.

Example 25

Preparation of Ticagrelor D-Tartrate

Ticagrelor (0.5 g) and acetone (10 mL) were charged into a round bottom flask and the mixture was stirred at about 30° C. for about 15 minutes for clear solution. Then D (−)-tartaric acid (0.16 g) was added to the above reaction mixture at about 30° C. and mixture was stirred for overnight. To the clear solution, n-hexane (35 mL) was added and stirred for about 1 hour at 25-30° C. for solid separation. The solid was filtered, washed with n-hexane (5 mL) and dried to afford the title compound in about 93% yield having chiral HPLC purity of about 98%.

Example 26

Preparation of Ticagrelor L-Tartrate

Ticagrelor (3 g) and acetone (60 mL) were charged into a round bottom flask and stirred at about 30° C. for about 10 minutes. The reaction mixture was filtered through hyflow bed followed by washing of the bed with acetone (10 mL). Then L (+)-tartaric acid (0.95 g) was added to the above filtrate at 30° C. and mixture was stirred for about 2 hours. The reaction mixture was cooled to 0-5° C. and maintained for about 30 minutes at the same temperature. The reaction mixture was concentrated up to 20% of its initial volume at 45° C. under reduced pressure. Then n-hexane (70 mL) was added to the reaction mixture and stirred for about 60 minutes for solid separation. The solid was isolated by filtration and dried at below 50° C. to afford the title compound in about 41.5% yield.

Example 27

Preparation of Ticagrelor O,O'-Di-p-Toluoyl-(2R,3R)-Tartaric Acid Salt

Ticagrelor (2 g) and acetone (40 mL) were charged into a round bottom flask and stirred at about 30° C. for about 15 minutes. The reaction mixture was filtered through hyflow bed followed by washing of the bed with acetone (10 mL). Then anhydrous (−) O,O'-di-p-toluoyl-(2R,3R)-tartaric acid (1.6 g) was added to the above filtrate at about 30° C. and mixture was stirred for about 1 hour. The reaction mixture was concentrated up to 20% of its initial volume at 45° C. under reduced pressure. Then n-hexane (100 mL) was added to the reaction mixture at 30° C. and stirred for about 2 hours for solid separation. The solid was isolated by filtration and dried at below 50° C. to afford the title compound in about 34.6% yield.

Example 28

Preparation of Ticagrelor Malonate

Ticagrelor (2 g) and acetone (40 mL) were charged into a round bottom flask and stirred at 30° C. for about 15 minutes. The reaction mixture was filtered through hyflow bed followed by washing of the bed with acetone (10 mL). Then malonic acid (0.44 g) was added to the above filtrate at about 30° C. and mixture was stirred for about 1 hour. The reaction mixture was concentrated up to 20% of its initial volume at 45° C. under reduced pressure. Then n-hexane (100 mL) was added to the reaction mixture at about 30° C. and stirred for about 90 minutes for solid separation. The solid was isolated by filtration and dried at below 50° C. to afford the title compound in about 46% yield having HPLC purity of about 98%.

Example 29

Preparation of Ticagrelor Oxalate

Ticagrelor (2 g) and acetone (40 mL) were charged into a round bottom flask and stirred at about 30° C. for about 15 minutes. The reaction mixture was filtered through hyflow bed followed by washing of the bed with acetone (10 mL). Then oxalic acid (0.38 g) was added to the above filtrate at about 30° C. and mixture was stirred for about 1 hour. The reaction mixture was concentrated up to 20% of its initial volume at 45° C. under reduced pressure. Then n-hexane (100 mL) was added to the reaction mixture at about 30° C. and mixture was stirred for about 3 hours to afford the title compound.

Example 30

Preparation of Ticagrelor Maleate

Ticagrelor (2 g) and acetone (40 mL) were charged into a round bottom flask and stirred at about 30° C. for about 15 minutes. The reaction mixture was filtered through hyflow bed followed by washing of the bed with acetone (10 mL). Then maleic acid (0.49 g) was added to the above filtrate at about 30° C. and mixture was stirred for about 1 hour. The reaction mixture was concentrated up to 20% of its initial volume at 45° C. under reduced pressure. Then n-hexane (100 mL) was added to the reaction mixture at about 35° C. and mixture was stirred for about 3 hours to afford the title compound.

Example 31

Preparation of Ticagrelor Citrate

Ticagrelor (1 g) and acetone (20 mL) were charged into a round bottom flask and stirred at about 30° C. for about 20 minutes. The reaction mixture was filtered through hyflow bed followed by washing of the bed with acetone (5 mL). Then citric acid (0.44 g) was added to the above filtrate at about 30° C. and mixture was stirred for about 1 hour. The reaction mixture was concentrated up to 20% of its initial volume at about 40° C. under reduced pressure. Then n-hexane (50 mL) was added to the reaction mixture at about 30° C. and mixture was stirred for about 2 hours to afford the title compound.

Example 32

Preparation of Ticagrelor

Ticagrelor malonate (0.5 g) and ethyl acetate (10 mL) were charged into round bottom flask. To the mixture 10% aqueous sodium carbonate solution (50 mL) was added and mixture was stirred for 15 minutes. The layers were separated and organic layer was subjected to distillation under vacuum to afford the title compound.

Example 33

Preparation of Ticagrelor Solid Dispersion with PVP (1:1 w/w)

To a solution of Ticagrelor (1 g) in methanol (20 mL), polyvinylpyrrolidone (1 g) was added. The mixture was stirred for clear solution at 25-30° C. Then solvent from the mixture was evaporated under reduced pressure to dryness to afford the solid. The resulting dispersion was found to be amorphous by X-ray powder diffraction.

Example 30

Pharmaceutical Composition of Ticagrelor

A pharmaceutical composition of Ticagrelor is prepared by using the following ingredients:

| Ingredients | mg/tab |
|---|---|
| Ticagrelor | 90.0 |
| Polyvinylpyrrolidone | 30.0 |
| Mannitol | 45.0 |
| Dibasic calcium phosphate dihydrate | 15.0 |
| Sodium starch glycolate | 6.0 |
| Magnesium stearate | 3.0 |

Ticagrelor and polyvinylpyrrolidone are dissolved in methanol to form a solution. Methanol is then evaporated resulting in an amorphous solid dispersion of ticagrelor in powder form which is further milled. Obtained solid dispersion of ticagrelor is then blended with mannitol, dibasic calcium phosphate dihydrate, sodium starch glycolate and mixed for 3 minutes. The blend is then lubricated with magnesium stearate and compressed into tablets.

The invention claimed is:

1. A process for preparing a compound of Formula I or pharmaceutically acceptable salts thereof,

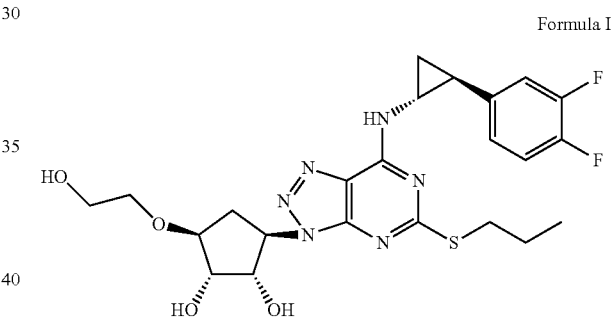

Formula I comprising,
a) reacting the compound of Formula III or a salt thereof with a compound of Formula II or a salt thereof, in presence of a base in a suitable polar solvent comprising of, polar aprotic solvents, water or mixtures thereof, to prepare a compound of Formula IV or a salt thereof,

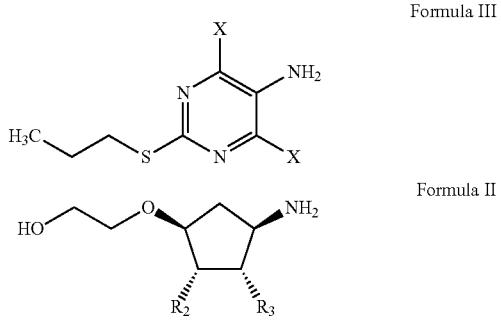

Formula III

Formula II

Formula IV

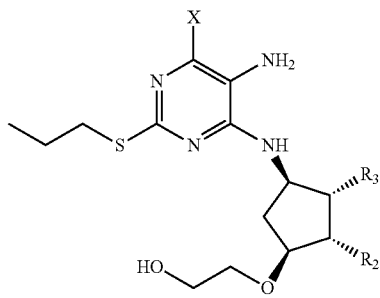

where R₂ and R₃ independently are hydroxy or protected hydroxy groups, X is halogen, b) converting the compound of Formula IV or a salt thereof to compound of Formula I or pharmaceutically acceptable salts thereof.

2. The process according to claim 1, wherein compound of Formula II is present in the form of L-tartrate salt.

3. The process according to claim 1, wherein suitable polar solvent is selected from dimethyl sulfoxide, water or any mixtures thereof.

4. The process according to claim 1, wherein the solvent is water and the base is sodium bicarbonate.

5. The process according to claim 1, wherein the base is selected from triethyl amine, diisopropyl ethylamine, sodium bicarbonate, potassium carbonate.

6. The process according to claim 5, wherein the base is sodium bicarbonate.

7. The process according to claim 1, wherein the reaction is carried out at any temperature in the range of 60-140° C.

8. The process according to claim 1, wherein after completion of reaction compound of Formula IV is isolated by using suitable solvent comprising aromatic hydrocarbon, esters, ketones, aliphatic hydrocarbons, water or mixtures thereof.

9. The process according to claim 8, wherein suitable solvent is toluene, ethyl acetate, and their combinations with hexane or heptane.

10. The process according to claim 1 further comprising,
   a) cyclization of a compound of Formula IV or its salt in presence of sodium nitrite and suitable acid in a suitable solvent, to afford a compound of Formula V, Formula IV

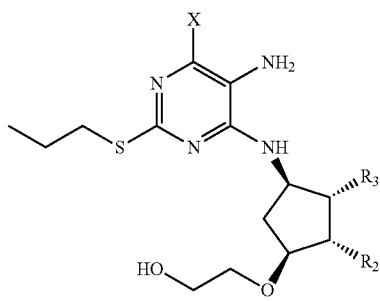

Formula V

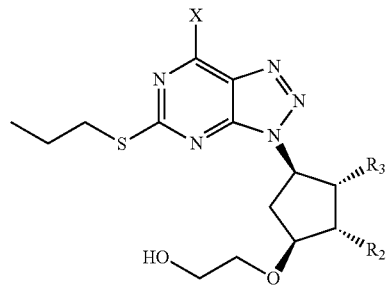

where R₂ and R₃ independently are hydroxy or protected hydroxy groups and X is halogen, b) reaction of a compound of Formula V with the compound of Formula VIIa, or a salt thereof, to form a compound of Formula VI, Formula V

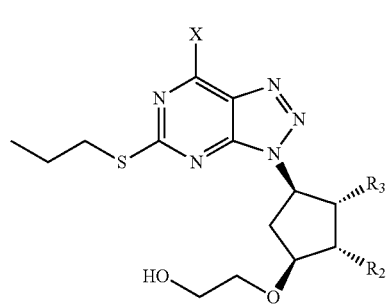

Formula VIIa

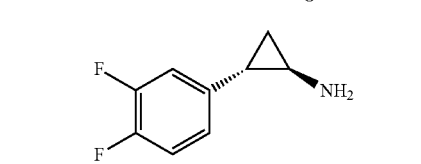

Formula VI

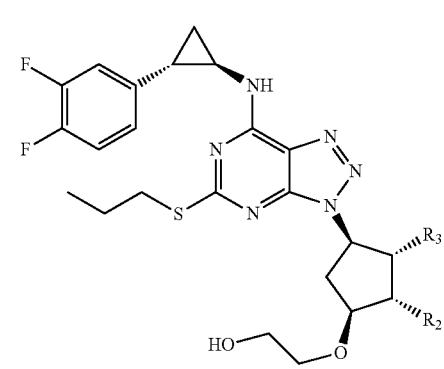

where R₂ and R₃ independently are hydroxy or protected hydroxy groups and X is halogen, c) deprotection of the compound of Formula VI under suitable conditions to afford Ticagrelor of Formula I.

* * * * *